United States Patent
Gielen et al.

(10) Patent No.: US 8,150,497 B2
(45) Date of Patent: Apr. 3, 2012

(54) SYSTEM FOR NAVIGATING A PLANNED PROCEDURE WITHIN A BODY

(75) Inventors: Frans L. H. Gielen, Eckelrade (NL); Frank Hertel, Besslich-Newel (DE); Peter Gemmar, Trier (DE); Peter Appenrodt, Bremen (DE)

(73) Assignee: Medtronic, Inc., Minneapolis, MN (US)

( * ) Notice: Subject to any disclaimer, the term of this patent is extended or adjusted under 35 U.S.C. 154(b) by 1161 days.

(21) Appl. No.: 11/584,422

(22) Filed: Oct. 20, 2006

(65) Prior Publication Data

US 2008/0097187 A1 Apr. 24, 2008

Related U.S. Application Data

(60) Provisional application No. 60/843,441, filed on Sep. 8, 2006, provisional application No. 60/843,440, filed on Sep. 8, 2006, provisional application No. 60/843,435, filed on Sep. 8, 2006, provisional application No. 60/843,434, filed on Sep. 8, 2006.

(51) Int. Cl.
*A61B 5/05* (2006.01)

(52) U.S. Cl. ........ 600/427; 600/103; 600/117; 600/407; 600/426; 600/429; 382/128; 382/154; 606/130

(58) Field of Classification Search .................. 600/103, 600/117, 407, 426, 427, 429; 382/128, 154; 606/130
See application file for complete search history.

(56) References Cited

U.S. PATENT DOCUMENTS

| | | | |
|---|---|---|---|
| 4,961,425 A | 10/1990 | Kennedy et al. |
| 5,185,809 A | 2/1993 | Kennedy et al. |
| 5,390,258 A | 2/1995 | Levin |
| 5,531,227 A | 7/1996 | Schneider |
| 5,546,472 A | 8/1996 | Levin |
| 5,592,939 A | 1/1997 | Martinelli |
| 5,613,013 A | 3/1997 | Schuette |
| 5,638,819 A | 6/1997 | Manwaring et al. |
| 5,740,808 A | 4/1998 | Panescu et al. |
| 5,913,820 A | 6/1999 | Bladen et al. |
| 5,983,126 A | 11/1999 | Wittkampf et al. |
| 6,240,308 B1 | 5/2001 | Hardy et al. |
| 6,246,784 B1 | 6/2001 | Summers et al. |
| 6,314,556 B1 | 11/2001 | DeBusk et al. |
| 6,351,573 B1 | 2/2002 | Schneider |
| 6,381,485 B1 | 4/2002 | Hunter et al. |
| 6,390,097 B1 | 5/2002 | Chandra |
| 6,474,341 B1 | 11/2002 | Hunter et al. |
| 6,482,182 B1 | 11/2002 | Carroll et al. |

(Continued)

FOREIGN PATENT DOCUMENTS

WO WO-92/22243 12/1992

(Continued)

OTHER PUBLICATIONS

Brummer et al, "Hough transform detection of the longitudinal fissure in tomographic head images", IEEE Trans Med Imaging, vol. 10(1), pg. 74-81, 1991.*

(Continued)

*Primary Examiner* — Brian Casler
*Assistant Examiner* — Joseph M Santos
(74) *Attorney, Agent, or Firm* — Harness, Dickey & Pierce

(57) ABSTRACT

A system including a processor and/or processor system can be used to create a plan for a procedure, such as a surgical procedure. The plan for the surgical procedure can be based on various elements, including determined anatomical landmarks that can be used to determine anatomical targets of a patient. The planning processor can be used to determine the anatomical landmarks and identify anatomical targets in image data of a subject, even if the anatomical targets are indistinguishable in the image data.

28 Claims, 8 Drawing Sheets

U.S. PATENT DOCUMENTS

| | | | |
|---|---|---|---|
| 6,493,573 | B1 | 12/2002 | Martinelli et al. |
| 6,516,212 | B1 | 2/2003 | Bladen et al. |
| 6,529,758 | B2 | 3/2003 | Shahidi |
| 6,574,356 | B1 | 6/2003 | Lee et al. |
| 6,611,615 | B1 | 8/2003 | Christensen |
| 6,697,534 | B1 | 2/2004 | Tan et al. |
| 7,167,760 | B2 | 1/2007 | Dawant et al. |
| 2001/0040991 | A1 | 11/2001 | Asano et al. |
| 2003/0078485 | A1 | 4/2003 | Hartlep |
| 2003/0093004 | A1 | 5/2003 | Sosa et al. |
| 2003/0114752 | A1 | 6/2003 | Henderson et al. |
| 2003/0142857 | A1 | 7/2003 | Alyassin |
| 2003/0152262 | A1 | 8/2003 | Mao et al. |
| 2004/0049121 | A1* | 3/2004 | Yaron ............................ 600/544 |
| 2004/0215071 | A1 | 10/2004 | Frank et al. |
| 2005/0004617 | A1 | 1/2005 | Dawant et al. |
| 2005/0049486 | A1 | 3/2005 | Urquhart et al. |
| 2005/0070781 | A1* | 3/2005 | Dawant et al. ................ 600/407 |
| 2005/0085714 | A1 | 4/2005 | Foley et al. |
| 2005/0085720 | A1 | 4/2005 | Jascob et al. |
| 2005/0165294 | A1 | 7/2005 | Weiss |
| 2006/0084867 | A1 | 4/2006 | Tremblay et al. |
| 2006/0270926 | A1 | 11/2006 | Hu et al. |
| 2007/0244387 | A1* | 10/2007 | Rodriguez Ponce et al. . 600/411 |
| 2008/0123921 | A1 | 5/2008 | Gielen et al. |
| 2008/0123922 | A1 | 5/2008 | Gielen et al. |
| 2008/0123923 | A1 | 5/2008 | Gielen et al. |

FOREIGN PATENT DOCUMENTS

| | | |
|---|---|---|
| WO | WO-95/20343 | 8/1995 |
| WO | WO-96/04614 | 2/1996 |
| WO | WO-98/38908 | 9/1998 |
| WO | WO-99/10816 | 3/1999 |
| WO | WO-01/01346 | 1/2001 |
| WO | WO-02/43003 | 5/2002 |
| WO | WO-2004/077359 | 9/2004 |
| WO | WO-2004077359 | 9/2004 |
| WO | WO-2004/096018 | 11/2004 |
| WO | WO-2005/002444 | 1/2005 |
| WO | WO-2005/048844 | 6/2005 |

OTHER PUBLICATIONS

"Anatomic Labelling of PET Brain Images with Automatic Detection of AC and PC," Yu, et al., Journal of Digital Imaging, vol. 11, No. 3, Suppl 1 (Aug.) 1998, pp. 56-58.

"Automatic Detection of the Mid-Sagittal Plane in 3-D Brain Images," Ardekani, et al., IEEE Transactions on Medical Imaging, vol. 16, No. 6, Dec. 1997, pp. 947-952.

"Automatic Estimation of Midsagittal Plane and AC-PC Alignment Based on Nonrigid Registration", Anbazhagan et al., Third IEEE International Symposium on Biomedical Imaging (ISBI 2006), Apr. 6-9, 2006, Arlington, VA (4 pages).

"Automatic Registration of Brain Magnetic Resonance Images Based on Talairach Reference System," Han, et al., Journal of Magnetic Resonance Imaging 20:572-580 (2004). Copyright 2004 Wiley-Liss, Inc.

"Creation and Use of a Talairach—Compatible Atlas for Accurate, Automated, Nonlinear Intersubject Registration, and Analysis of Functional Imaging Data," Woods, et al., Human Brain Mapping 8:73-79(1999); Copyright 1999, Wiley-Liss, Inc.

"Efficient and Reliable Schemes for Nonlinear Diffusion Filtering," Weickert, et al., IEEE Transactions on Image Processing, 7(3):398-410, 1998.

"Free Software Tools for Atlas-based Volumetric Neuroimage Analysis", Bazin et al, , Proceedings of SPIE Medical Imaging 2005: Image Processing vol. 5747, pp. 1824-1833, in San Diego, CA, Feb. 12-17, 2005.

"Fully Automatic Identification of AC and PC Landmarks on Brain MRI Using Scene Analysis," Verard, et al., IEEE Transactions on Medical Imaging, vol. 16, No. 5, Oct. 1997, pp. 610-616.

"Galileo BrainGuide™, Galileo LungGuide™", Medical Diagnostics Exchange Corp., 2004 MDX Corp. (6 pages).

"Landmark—based Registration and Measurement of Magnetic Resonance Images: A Reliability Study," Arndt, et al., Psychiatry Research: Neuroimaging 67 (1996) 145-154, copyright 1996 Elsevier Science Ireland, Ltd.

Medtronic, StimPilot™ Procedure Pocket Guide, 2005 Medtronic Navigation 9732131, Revision 3 (67 pages), copyright 2005.

"M I P A V, Medical Image Processing Analysis, & Visualization,Technical Guide 1, Labeling and Measuring Brain Components in Talairach Space", National Institutes of Health Center for Information Technology, Rockville, Maryland, Jul. 12, 2005 (64 pages).

"Parallel Implementations of AOS Schemes: A Fast Way of Nonlinear Diffusion Filtering," Weickert, et al., IEEE International Conference on Image Processing, 3:396-399, 1997.

"Talairach coordinates, atlases and segmentation: how to label and measure structures using MIPAV", Bazin, Laboratory for Medical Image Computing, Johns Hopkins University, printed from web site at http://mipav.cit.nih.gov/documentation/ presentations/talairach.pdf, publication date May 23, 2005 (27 pages).

"Truly 3D Midsagittal Plane Extraction for Robust Neuroimage Registration", Teverovskiy et al., Robotics Institute, Carnegie Mellon University, Mar. 2004 (24 pages).

International Search Report mailed Jun. 18, 2007 for PCT/US2007/001837 claiming benefit of U.S. Appl. No. 60/843,441, filed Sep. 8, 2006; U.S. Appl. No. 60/843,440, filed Sep. 8, 2006; U.S. Appl. No. 60/843,435, filed Sep. 8, 2006; U.S. Appl. 60/843,434, filed Sep. 8, 2006; U.S. Appl. No. 11/584,814, filed Oct. 20, 2006; U.S. Appl. No. 11/584,423, filed Oct. 20, 2006; U.S. Appl. No. 11/584,813, filed Oct. 20, 2006; and U.S. Appl. No. 11/584,422, filed Oct. 20, 2006.

International Search Report mailed Jun. 20, 2007 for PCT/US2007/001838 claiming benefit of U.S. Appl. No. 60/843,441, filed Sep. 8, 2006; U.S. Appl. No. 60/843,440, filed Sep. 8, 2006; U.S. Appl. No. 60/843,435, filed Sep. 8, 2006; U.S. Appl. No. 60/843434, filed Sep. 8, 2006; U.S. Appl. No. 11/584,814, filed Oct. 20, 2006; U.S. Appl. No. 11/584,423, filed Oct. 20, 2006; U.S. Appl. No. 11/584,813, filed Oct. 20, 2006; and U.S. Appl. No. 11/584,422, filed Oct. 20, 2006.

"Automatic Path Searching for Minimally Invasive Neurosurgical Planning," Fujii, T., et al., Proceedings of the SPIE—The International Society for Optical Engineering SPIE—Int. Soc. Opt. Eng. USA, vol. 4681, 2002, pp. 527-538, XP002435813.

"Optimization of Tissue Segmentation of Brain MR Images Based on Multispectral 3D Feature Maps," Mohamed, F.B., et al., Magnetic Resonance Imaging, Tarrytown, NY, USA, vol. 17, No. 3, Apr. 1999, pp. 403-409, XP001153256.

Finnis, Kirk W., et al., "Three-Dimensional Database of Subcortical Electrophysiology for Image-Guided Stereotactic Functional Neurosurgery," IEEE Transactions of Medical Imaging, vol. 22, No. 1 (Jan. 2003) pp. 93-104.

Advisory Action mailed May 31, 2011 for U.S. Appl. No. 11/584,814.

Examiner Interview Summary Record (PTOL-413) mailed Feb. 3, 2010 for U.S. Appl. No. 11/584,813.

Examiner Interview Summary Record (PTOL-413) mailed Jun. 3, 2011 for U.S. Appl. No. 11/584,814.

Examiner Interview Summary Record (PTOL-413) mailed Mar. 11, 2010 for U.S. Appl. No. 11/584,814.

Office Action (Final Rejection) mailed Jun. 14, 2010 for U.S. Appl. No. 11/584,813.

Office Action (Final Rejection) mailed Mar. 2, 2011 for U.S. Appl. No. 11/584,814.

Office Action (Final Rejection) mailed Mar. 30, 2011 for U.S. Appl. No. 11/584,423.

Office Action (Non-Final Rejection) mailed Aug. 5, 2010 for U.S. Appl. No. 11/584,423.

Office Action (Non-Final Rejection) mailed Dec. 15, 2009 for U.S. Appl. No. 11/584,814.

Office Action (Non-Final Rejection) mailed Jun. 23, 2010 for U.S. Appl. No. 11/584,814.

Office Action (Non-Final Rejection) mailed Nov. 12, 2009 for U.S. Appl. No. 11/584,813.

Rohde, Gustavo K., et al. "The Adaptive Bases Algorithm for Intensity—Based Nonrigid Image Registration." IEEE Transactions on Medical Imaging, vol. 22, No. 11 (Nov. 2003) pp. 1470-1479.

* cited by examiner

SYSTEM FOR NAVIGATING A PLANNED PROCEDURE WITHIN A BODY

This application claims the benefit of U.S. Provisional Ser. No. 60/843,441, filed Sep. 8, 2006; U.S. Provisional Ser. No. 60/843,440, filed, Sep. 8, 2006; U.S. Provisional Ser. No. 60/843,435, filed Sep. 8, 2006; and U.S. Provisional Ser. No. 60/843,434, filed Sep. 8, 2006 and is filed concurrently with U.S. patent application Ser. No. 11/584,814 entitled "METHOD FOR IDENTIFICATION OF ANATOMICAL LANDMARKS", U.S. patent application Ser. No. 11/584,423 entitled, "SYSTEM FOR IDENTIFICATION OF ANATOMICAL LANDMARKS", and U.S. patent application Ser. No. 11/584,813 entitled, "METHOD FOR PLANNING A SURGICAL PROCEDURE". The disclosures of the above applications are incorporated herein by reference.

FIELD

The present disclosure relates to a surgical procedure, and particularly to a computer assisted surgical system for navigating a procedure within a body.

BACKGROUND

The statements in this section merely provide background information related to the present disclosure and may not constitute prior art.

Surgical procedures are often performed by skilled individuals, such as physicians. The physicians can perform various surgical procedures based upon their training and past experience, augmented by study of a particular patient. Nevertheless, various portions of a particular patient may be difficult to examine or identify depending upon the area of the anatomy to be examined and the positioning of the patient.

Surgical procedures where these difficulties may arise can include various neurosurgical procedures that affect various functions of the brain. For example, a tumor or growth may be removed from a brain. Other procedures, however, may be performed to augment a portion of the brain without removing a portion of the brain, affecting surrounding tissue in the brain, or without visual cues of differences between the area of the brain to be affected and surrounding areas.

For example, certain neurological procedures can be performed that affect "functional targets". The functional targets can be portions of the brain that naturally affect or control various portions of the anatomy but are, for various reasons, damaged. These functional targets in the brain can be stimulated through procedures such as deep brain stimulation. Functional targets, even if malfunctioning in a particular manner, may not differ anatomically or visually from the surrounding tissues. Therefore, it is desirable to provide a system that is able to determine the position of a functional target in the brain.

SUMMARY

A computer assisted surgical system or navigation system can be used to determine a portion of anatomy, such as a portion in a brain, that may not be visually distinct from surrounding tissue portions. It will be understood that although a system can determine a particular region of a brain, it can also be used to determine a position of other portions of the anatomy. In one example, various imaging techniques, such as magnetic resonance imaging (MRI) can be used to obtain a detailed image of the brain. A system is provided that can determine various anatomical or functional targets based upon landmarks in the brain, plan a route or trajectory to reach the selected anatomical targets, and determine a point of entry to reach the anatomical target. The system can be fully automatic and include a processor to execute instructions to determine the anatomical targets. The system can also be combined with manual inputs. The anatomical target can include a functional target which can be a portion of the brain that controls a certain function of the anatomy. Although it will be understood that a similar system can be used to obtain access or determine a position of a tumor, a damaged region of the brain, portions of the brain based upon an anatomical landmarks, or other portions of the anatomy.

According to various embodiments a system to navigate a surgical plan relative to an anatomy is taught. The system can include an instrument operable to assist in the performance of the surgical plan, a tracking device operable to be interconnected with the instrument, and a tracking system operable to track the tracking device wherein a location of the instrument is operable to be determined at least in part based upon the tracked position of the tracking device. The system can also include a planning processor operable to execute instructions. The instructions can include identifying an anatomical landmark in an image data of the anatomy, determining an anatomical target based upon the anatomical landmark, and determining a path through the anatomy based upon the image data of the anatomy to reach the anatomical target. The system can also include a display to display at least one of a planned path, an icon illustrating the position of the instrument, an icon illustrating the entire path of the instrument to an instant in time, the image data of the anatomy, or combinations thereof.

According to various embodiments a system to navigate a surgical plan relative to an anatomy is taught. The system can include an instrument operable to assist in the performance of the surgical plan, a tracking device operable to be interconnected with the instrument at a leading end of the instrument, and a tracking system operable to track the tracking device wherein a location of the instrument is operable to be determined at least in part based upon the tracked position of the tracking device. The system can also include a memory system that can store a plan to be performed at least in part with the instrument and including image data of the anatomy with an identified anatomical landmark. Also, a display operable to display at least one of a planned path, an icon illustrating the navigated position of the instrument, an icon illustrating the entire path of the instrument to an instant in time, and image data of the anatomy. The plan store in the memory system can include at least one of determining the location of a mid-sagittal plane, determining the location of an anterior commissure, determining the location of a posterior commissure, aligning a plurality of slices of the anatomy based upon the determined mid-sagittal plane, a trajectory of the instrument, or combinations thereof.

According to various embodiments a system to navigate a plan relative to an anatomy and determine whether a plan to reach a target is performed is taught. The system can include an instrument operable to assist in the performance of the surgical plan, a tracking device operable to be interconnected with the instrument at a leading end of the instrument, and a tracking system operable to track the tracking device wherein a location of the instrument is operable to be determined at least in part based upon the tracked position of the tracking device. The system can further include an imaging system operable to obtain an image data of the anatomy. Also, a planning processor can be provided that can execute instructions. The instructions can identify an anatomical landmark, determine an anatomical target based upon the anatomical landmark, or determine a path through an anatomical region based upon image data to reach the anatomical target. Also, a display can display at least one of a planned path, an icon illustrating the position of the instrument, an icon illustrating the entire path of the instrument to an instant in time, image data of the anatomy, or combinations thereof.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION OF VARIOUS EMBODIMENTS

The following description is merely exemplary in nature and is not intended to limit the present disclosure, application, or uses. Though the following teachings relate to a method and apparatus for use with a neurosurgical procedure, this is merely exemplary and not intended to limit the scope of the present disclosure.

Identifying various structures of an anatomy, such as portions of the neuroanatomy, can be useful for performing selected procedures on a brain, such as deep brain stimulation (DBS), ablation, tumor removal, drug delivery, gene therapy, cell delivery therapy, needle delivery, implant delivery, lead or electrode delivery, and the like. The identification of various brain structures can be difficult based on the location, size, activity, and other factors. For example, identifying the location of the sub-thalamic nucleus (STN) can be difficult based upon its location within the brain and its visual similarity to the area surrounding it. In particular, the STN may appear substantially similar to the brain tissue surrounding the STN in a patient, even if the STN or related portions of the brain are diseased. Nevertheless, the STN can define a functional target that may be acted upon to achieve a precise or selected result. It has been discovered that the STN can, however, generally be precisely located based upon its location relative to identifiable anatomical portions of the brain. According to the present disclosure, the STN can be located based upon a determination or identification of the anterior commissure (AC) and posterior commissure (PC). Thus, treatments such as DBS can be applied to the STN to treat a disease, such as Parkinson's.

Figure 1:
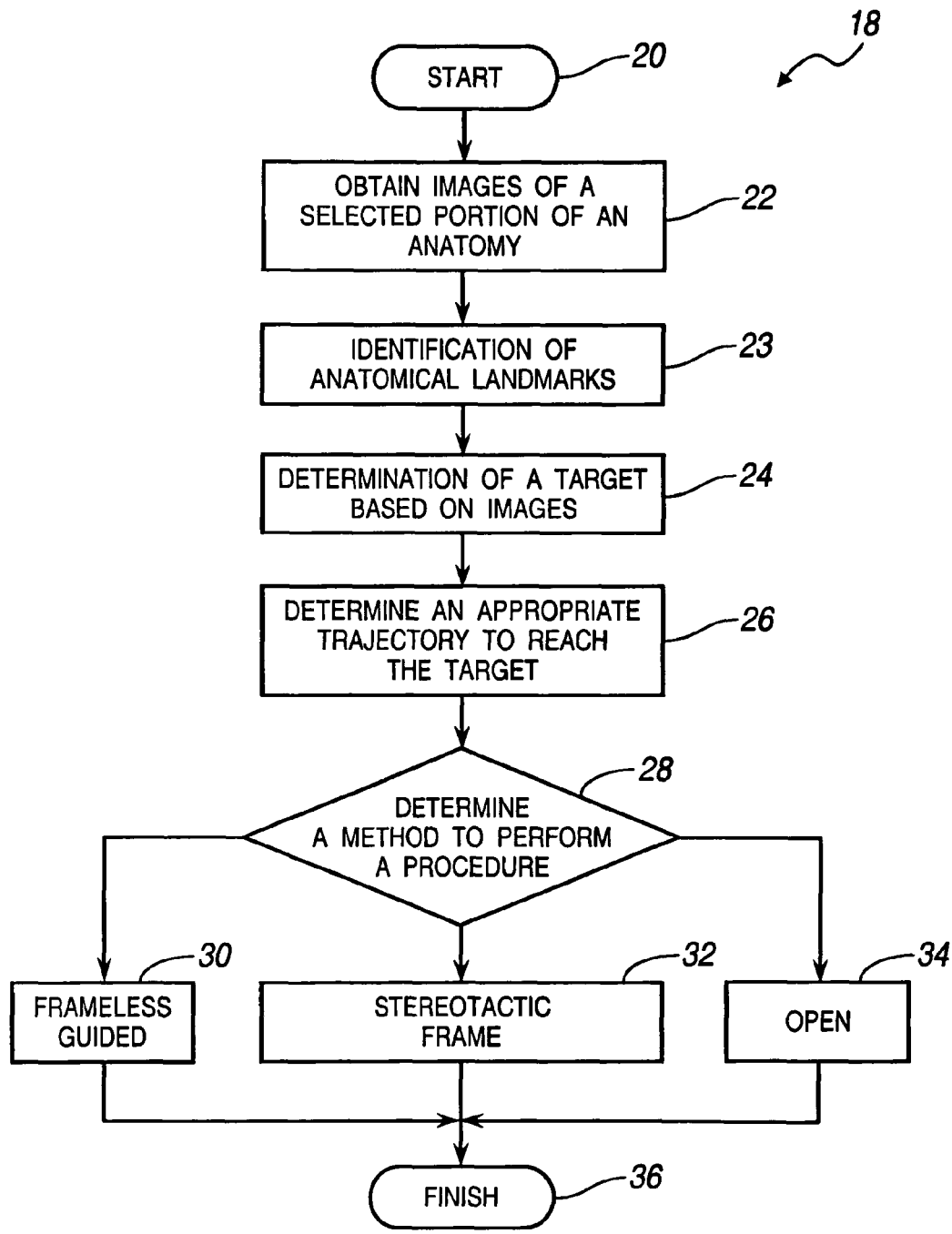
FIG. 1 is a flowchart illustrating a method of performing a surgical procedure.

With initial reference to FIG. 1, a guided procedure 18 is broadly described and illustrated. The guided procedure 18 can be used for various types of procedures, as discussed herein, such as an image guided or navigated procedure, a physically guided procedure (e.g., a stereotactic frame), or a user or visually guided procedure. Therefore, the guided procedure 18 will be understood to be a process that allows for a user or a system to perform a procedure based upon identification of various anatomical landmarks, anatomical targets, plans, or trajectories and the like. Generally, the guided procedure 18 can begin in block 20 which is a start block. Images can be obtained of the selected portion of the anatomy in block 22. The selected portion of the anatomy can be any appropriate portion of the anatomy, such as a brain and skull. It will be understood that images can be obtained in any appropriate manner such as multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative CT, single photo emission computed tomography (SPECT), planar gamma scintigraphy (PGS), or any other appropriate type of image data or combinations thereof, including those discussed further herein. It will also be understood that a general or patient specific or matched atlas can be used. This can be helpful to decrease the number of patient specific images required while maintain accuracy and quantity of image data.

The guided procedure 18, after image data is obtained in block 22, can be used to identify anatomical landmarks in block 23 in the area in the area where the image data was obtained. The anatomical landmarks can be identified according to any appropriate procedures, as discussed herein. The anatomical landmarks can also be used to determine the position of anatomical or fractional targets, as discussed in relation to block 24. The anatomical landmarks can be physically identifiable landmarks, image identifiable landmarks, or any appropriate landmark. The anatomical targets, discussed herein, can be physical targets, functional targets, or any appropriate target.

The determination of anatomical targets based on the obtained images and the identified or determined landmarks in block 23 can be performed in block 24. Once the targets are determined in block 24, a determination of an appropriate trajectory to reach the target can be determined in block 26. Then a determination of a method to perform the procedure can be determined in block 28. Various exemplary methods of performing the procedure can include a frameless guided procedure in block 30, a stereotactic frame procedure in block 32, or a substantially open procedure in block 34. Then the procedure can be finished in block 36 including procedures such as closing the incision, removing the stereotactic frame from the patient, etc. It will be understood that various other portions can be added to the guided method 18 based upon the patient, physician choice, or the like.

Identification of landmarks 23, detection of targets in block 24 based on images and determination of trajectory in block 26 to reach a target can, in its broadest sense, summarize the guided procedure 18. In other words, the guided procedure 18 generally includes determination of targets on which a procedure can be performed, and a determination of a trajectory or path to reach the target based upon an entry point and the final target. The target can be any appropriate target (e.g., a functional target within the brain) and the trajectory can include any appropriate path (e.g., a straight path, a curved path, or combinations thereof).

Further, it will be understood that the various procedures that can be performed, such as a frameless guided procedure in block 30, a stereotactic frame procedure in block 32, or a substantially open procedure in block 34, can be performed according to any appropriate method and with any appropriate instruments. For example, the substantially frameless guided procedure can be performed with the assistance of various systems such as the AxiEM™ system provided by Medtronic Navigation, Inc. The AxiEM™ system can use trackable instruments and trackable markers to track a location of a portion of the anatomy relative to an instrument. A stereotactic frame procedure can be performed with any appropriate instrument such as the StimPilot™ of Medtronic Navigation, Inc. The StimPilot™ device can use both guided instruments and a stereotactic frame, which can also be tracked, to determine a location of the frame, the instrument, and a patient. Also tracked frame systems can include those disclosed in U.S. patent application Ser. No. 10/651,267, now U.S. Pat. App. Pub. 2005/0049486, herein incorporated by reference. Also conventional stereotactic frames can be used, such as those discussed herein. Finally, a substantially open procedure can be performed if a navigated procedure is not desirable, available, or contraindicated. Nevertheless, it will be understood that the identification of landmarks, determination of targets and the determination of trajectories in blocks 23, 24, and 26 can assist a user, such as a physician, in performing an open procedure. It will also be understood that combinations of the various types of procedures can be performed depending upon the patient, user efficiency, and the like.

It will also be understood that the discussion herein relating to a procedure of determining a particular portion of a brain, such as the STN in a brain based upon the position of an AC and a PC, is merely exemplary of a selected procedure. The guided procedure 18 can also be performed for various reasons such as deep brain stimulation (DBS). It will be understood, however, that the guided procedure 18 and the various techniques and apparatuses described herein can be used for any appropriate procedure. Discussion in relation to a brain and the determination of the STN is merely exemplary and not intended to limit the scope of the present teachings. Further, it will be understood that any appropriate instruments can be used to perform a procedure in the various exemplary systems described herein and shall not limit the scope of appropriate systems.

As will be discussed further herein, the guided procedure 18 can be used in any appropriate portion of a procedure. For example, a planning phase for a procedure can be further supported and enhanced by the guided procedure 18 or the procedure can be performed with navigated instruments and the guided procedure 18 can be used to assure appropriate execution of the procedure. In particular, when planning a procedure, a user can use the guided procedure 18 to assist in identifying anatomical landmarks, determining an appropriate location of various anatomical targets, trajectories to reach an anatomical target, and entry points. This can assist a user, such as a surgeon, in innumerable ways, by assisting or standardizing a procedure, providing objective results, reducing the time and costs of a procedure, reducing the time and costs of identifying anatomical landmarks, determining trajectory and entry points, and determining other vital brain anatomy. The guided procedure 18 can also assist in determining an appropriate location of a treatment delivery device, identifying very specific portions of a selected anatomical target, or assisting in diagnosing a symptom or a disease. It will be understood that the appropriate treatment can also be assisted by providing a system to determine an appropriate location of a selected treatment and device. Various selected treatment planning systems can include those disclosed in U.S. patent application Ser. No. 10/651,267, now U.S. Pat. App. Pub. 2005/0049486, referenced above and commonly assigned.

It will be understood that the system and procedures discussed herein can provide assistance and standardize a surgical procedure in a number of ways and those discussed herein are merely exemplary. The guided procedure 18 can be provided as a set of instructions to be executed by a processor. The processor can, based on the instructions and certain data, identify or locate anatomical landmarks, locate targets and identify appropriate trajectories for an instrument.

The procedure 18 again begins in block 20 and proceeds to block 22 which includes obtaining image data of an anatomical region. The imaging can be of any appropriate type such as T1 weighted or T2 weighted MRI imaging. The imaging can be selected from other appropriate types of imaging, such as computer tomography (CT), PET, SPECT, ultrasound or any appropriate type. The imaging, such as MRI or CT imaging, can be performed with an appropriate slice thickness such as about 1 mm, 1.5 mm, 2 mm, or any appropriate thickness. The thickness and resolution of the imaging can be used to assist in selected procedures by increasing the resolution and clarity of the selected anatomical regions. Nevertheless, the appropriate imaging technique can be used to create selected images, such as two-dimensional or three-dimensional images of the patient. The images can be 256, 512, or any appropriate pixel number square or dimension. It will also be understood that the images may be any appropriate shape, for example rectangular. Also, the image data can include a resolution of any appropriate pixel count or pixels per area or length. The images produced with the appropriate imaging technique can then be used to assist or be used in the procedure 18.

The guided procedure 18 includes the identification of landmarks in block 23 and anatomical targets in block 24. These two blocks are further expanded in landmark and target (L&T) procedure 40, illustrated in FIG. 2. The L&T procedure 40 can be understood to be a subroutine or details of identification of landmarks in block 23 and the detection of targets in block 24. For example, after the image data are obtained in block 22, pre-processing of the image data can occur. The pre-processing can include various steps, as discussed herein, to improve quality of the image data and remove noise or artifacts from the image data. Various pre-processing steps can include identifying generally accepted anatomical regions or landmarks in the brain, or any portion of the anatomy, and the identification of selected targets.

The L&T process 40 can include smoothing or filtering the images in block 42. The image pre-processing and filtering can include known smoothing techniques such as linear Gaussian filtering, non-linear median filtering, and non-linear anisotropic diffusion. Although various smoothing techniques can be used, it may be selected to choose an appropriate technique that allows for both smoothing while maintaining edge detection and blurring in an appropriate manner and removing irrelevant details. In one smoothing technique, the known non-linear anisotropic diffusion can smooth gray values and image data using their gradients while not creating or destroying mass. Further, because the non-linear anisotropic diffusion is based on fluid techniques, it is based on the assumption that fluid is generally achieving an equilibrium state so that there is no diffusion over an edge and the edges are generally perpendicular. Briefly, the non-linear anisotropic diffusion is described by equation 1:

$$\frac{\partial u}{\partial t} = \nabla \cdot (D \cdot \nabla u) \quad (1)$$

where D is the diffusion tensor which is a positive symmetric matrix and t denotes the diffusion time. The diffusion tensor D possesses two orthonormal eigenvectors $v_1$ and $v_2$ described in equations 2 and 3 below:

$$v_1 \| \nabla u \quad (2)$$

$$v_2 \perp \nabla u \quad (3)$$

Each of the eigenvectors include corresponding eigenvalues $\lambda_1$ and $\lambda_2$ described in equations 4 and 5 below:

$$\lambda_1 := g(|\nabla u|^2) \quad (4)$$

$$\lambda_2 := 1. \quad (5)$$

The eigenvectors give the main diffusion direction and the corresponding eigenvalues the strength of the diffusion in the direction of the eigenvectors. The diffusion equation 1 can be used in various formats, such as a discrete form described for various schemes. Nevertheless, an optimized scheme can include the additive operator splitting scheme described in WEICKERT, J., B. M. TER HAAR ROMENY, M. A. VIERGEVER: *Efficient and Reliable Schemes for Nonlinear Diffusion Filtering*. IEEE Transactions on Image Processing, 7(3):398-410, 1998; and WEICKERT, J., K. J. ZUIDERVELD, B. M. TER HAAR ROMENY, W. J. NISSEN: *Parallel Implementations of AOS Schemes: A Fast Way of Nonlinear Diffusion Filtering*. IEEE International Conference on Image Processing, 3:396-399, 1997, both incorporated herein by reference. It will be understood that any appropriate scheme can be selected for any appropriate application and that the schemes described herein are merely exemplary.

Once the image data has been smoothed and filtered, the image data can be segmented with various techniques. The segmentation of the image data can be done for various reasons, such as with a brain scan, to determine various anatomical landmarks. For example, a 3-D segmentation of the third ventricle can be obtained in block 44. The 3-D segmentation can be performed in any appropriate manner such as with known region growing segmentation schemes, geometric active contour models, and various other appropriate techniques. Geometric models can be any appropriate models and can be based upon defining a front that evolves or changes according to a given curvature dependent speed function. Two different geometric models can be distinguished based upon the speed function, and can include the known level set method and the fast marching method. These known methods generally create or determine a segmentation by determining an initial front or contour and deforming it towards the object boundaries. A fundamental segmentation technique, however, can be any known region growing technique. Known region growing techniques can be used according to the present teachings to include determining a 3-D contour of a selected region beginning with a seed point, such as a voxel, datum, portion, pixel, etc., which can also be referred to as a seed voxel herein.

The 3-D segmentation of the third ventricle in an image of the brain can be formed according to any appropriate method such as a region growing method. The region growing method can begin with the seed voxel and expand therefrom into test points (e.g. voxels, datum, or portions) and herein referred to as "voxels" based on the difference between the test voxels touching the seed voxel and the seed voxel. In the pre-processed image data from block 42, which are generally three-dimensional image data, a voxel is a three-dimensional "pixel" defined by the image data. Therefore, the test voxels that touch a seed voxel have selected properties that can be compared to the seed voxel. For example, each voxel touching the seed voxel can become a test voxel and have a property (e.g. an intensity, color, contrast, or brightness) compared to the seed voxel. A distance of the property, such as the intensity) into the test voxel touching the seed voxel can been determined, and it can be determined how far an intensity similar to the average intensity of the seed voxel extends into the test voxel. If it is determined that the intensity extends a distance that is within a threshold distance into the test voxel, the test voxel can be added to the seed voxel, thus initiating a seed group or homogeneous region.

It will be also understood that the process can include adding a test voxel that has an appropriate intensity and is within a selected distance from the seed voxel. The appropriate intensity can be within a range of the seed voxel's intensity. For example, all test voxels can be added to the homogenous region that include a selected intensity that are no more than, for example, five voxels from the seed voxel. It will be understood that multiple techniques can be used to determine whether a test voxel should be added to a homogeneous region.

This process can then extend and continue until no more test voxels meet the threshold test, thus no conforming test voxels can be found. The non-conforming test voxel will include an intensity that is within a threshold intensity and within a threshold distance form the seed voxel. This process creates a homogeneous region that can be relatively simple to calculate. The homogeneous group can be one that defines the third ventricle. It will be understood that the technique used to define any homogeneous group (i.e. the third ventricle) is merely exemplary.

Further, the process can be fully automatic or be assisted by a manual user. The seed voxel can be automatically determined, manually determined, or combinations thereof. For example, a user can use an input device and a system, as discussed herein, to select a voxel as a seed voxel based on user knowledge such as relative location of the third ventricle. The system can then use the region growing method to determine the third ventricle. Alternatively, a system can select a voxel based on certain instructions such as intensity, location in the image data, etc. Furthermore, a system may select several possible seed voxels and a final choice can be made by a user. It will be understood, therefore, that the system can be substantially or completely automatic or be semi-automatic with the assistance of a user.

Figure 3A:
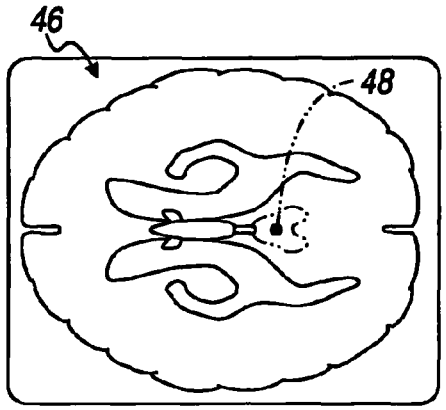
FIGS. 3A-3C illustrate, in succession, the segmentation of image data.
Figure 3B:
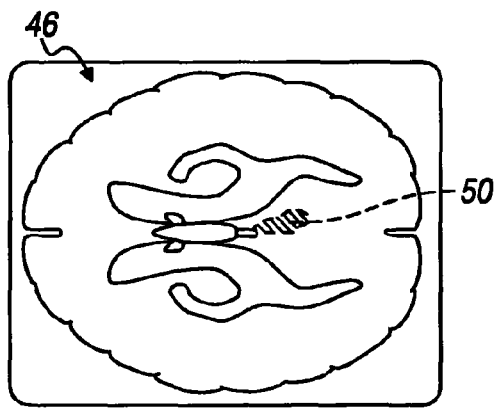
Figure 3C:
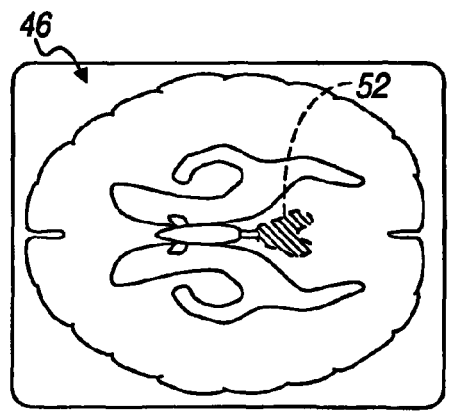

Briefly, as discussed above and illustrated in FIGS. 3A-3C, a smooth image data 46 can include a seed voxel 48. After partial progress of the grouping or homogeneity method, an initial or partial homogeneous region 50 is created, as illustrated in FIG. 3B. Finally, with reference to FIG. 3C, a finalized homogeneous region 52 is created. The final homogeneous region can be determined when the test voxel touching the current homogeneous region does not pass the threshold test. Therefore, the final homogeneous region 52 defines a homogeneous region in the image data which can be any appropriate region, such as the third ventricle illustrated in FIG. 3C. It will be understood that the illustration in FIG. 3C is substantially an axial view of the third ventricle and can be viewed from different perspectives due to the three-dimensional nature of the image data.

Returning to FIG. 2, the initially segmented image data from block 44 can be aligned or rotated in block 60. The alignment or rotation of the image data in block 60 can generally align the image data along the mid-sagittal plane (MSP) or any appropriate plane, as discussed further herein. This can also assist in the determination of an MSP from the image data. For example, it may be selected to align a plurality of images so that each of the images is substantially aligned for further calculation and display. It will be understood that the image data can be aligned for any appropriate reason or may not be aligned depending upon the selection of a user or the system. It can be selected to align the image data based upon further calculations or viewing by a user.

The alignment of the image data can be used for further calculations to assist in ensuring that each of the images are aligned in an appropriate manner. The alignment may be selected for various, for example the possibility that the images were taken with the patient in a substantially non-fixed manner may have allowed the images to be unaligned relative to one another. The alignment of the image in block 46 can ensure proper alignment of the multiple image data sets or image slices if the patient moved during the imaging process for the production of the various slices.

The third ventricle, which is segmented in block 24, is generally situated substantially near the center of the MSP and the MSP can define an appropriate symmetry of the brain. The segmentation of the third ventricle can, therefore, be used for the alignment process. The third ventricle can also be used to estimate the MSP for the alignment process. It will be understood, however, that the alignment may not be used according to various embodiments. As discussed further herein, a line can be determined based on the determined or identified third ventricle to assist in the alignment of the image data and/or slices.

The determination of the MSP can be based upon the segmented third ventricle through various techniques. For example, the segmented third ventricle can be skeletonized in each of the axial views of the image data. The skeletonization can include the successive thinning of the data defining the third ventricle to determine interconnected pixels that are only minimally connected to generally define a line. The line, or the terminating pixels of the line, is generally equal distance from the edge of the homogeneous group defined during the segmentation of the third ventricle that is segmented in block 44.

The sloping or misalignment of the MSP can then be calculated according to various techniques, such as the known Hough transform for line detection. The transform can be used to determine the axial slope angle and the coronal slope angle of the line defining the skeletonized line for the various ventricle interpretations. The whole sequence of MRI slices or images can then be rotated based upon the determined axial slope angles and coronal slope angles to substantially align the different images. The rotation or the alignment can be performed according to any appropriate manner such as bicubic interpolation.

The MSP can then be extracted from the aligned image data based upon an interpretation of the image data since the sagittal plane is formed or determined before the skeletonized lines in the aligned image data. Therefore, the MSP can be extracted from the image data to determine a substantially symmetrical line or plane within the image data for use in determination of various target points. The MSP is generally determined after the alignment of the data in block 60 so that the MSP is determined in block 62.

Figure 4A:
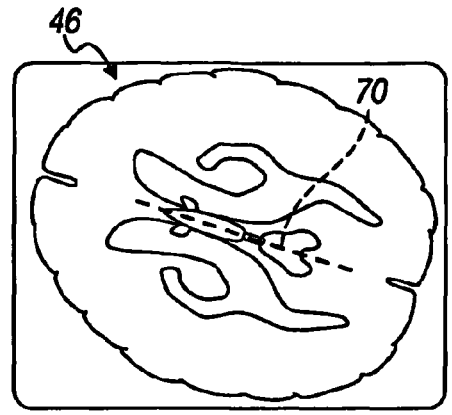
FIGS. 4A-4C illustrate, in sequence, alignment of various image data.
Figure 4B:
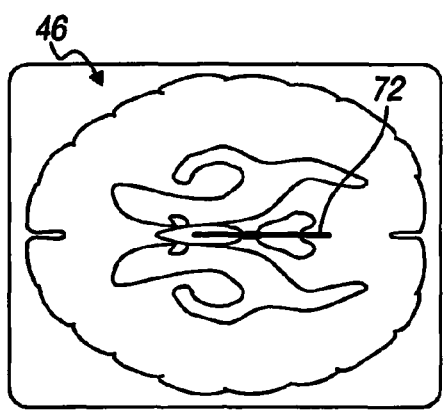
Figure 4C:
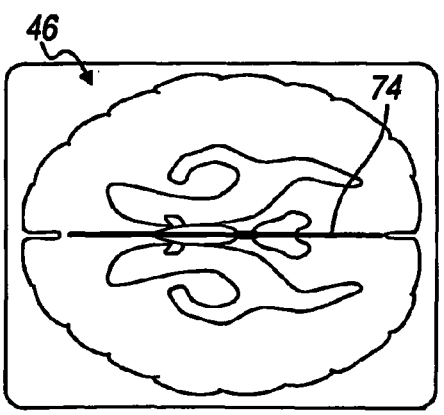

With brief reference to FIGS. 4A-4C, a skeletonized line 70 in the smoothed image data 46 can be determined according to the processes discussed above. The rotation of the skeletonized line can then generally form an aligned skeletonized line 72 within the image data 46, as illustrated in FIG. 4B. With reference to FIG. 4C, the skeletonized line can then be used to determine the MSP 74 in the image data 46. It will be understood that the description herein is merely exemplary and that the determination of the various anatomical regions can be determined in any appropriate manner. For example, the skeletonized line 72 can be determined relative to a plane including most of the segmented third ventricle in the image data slice. Also, the determination of the selected landmarks can be enhanced or made more efficient with an appropriate determination of a true axial plane thought he image data, such as with the MSP 74.

Figure 2:
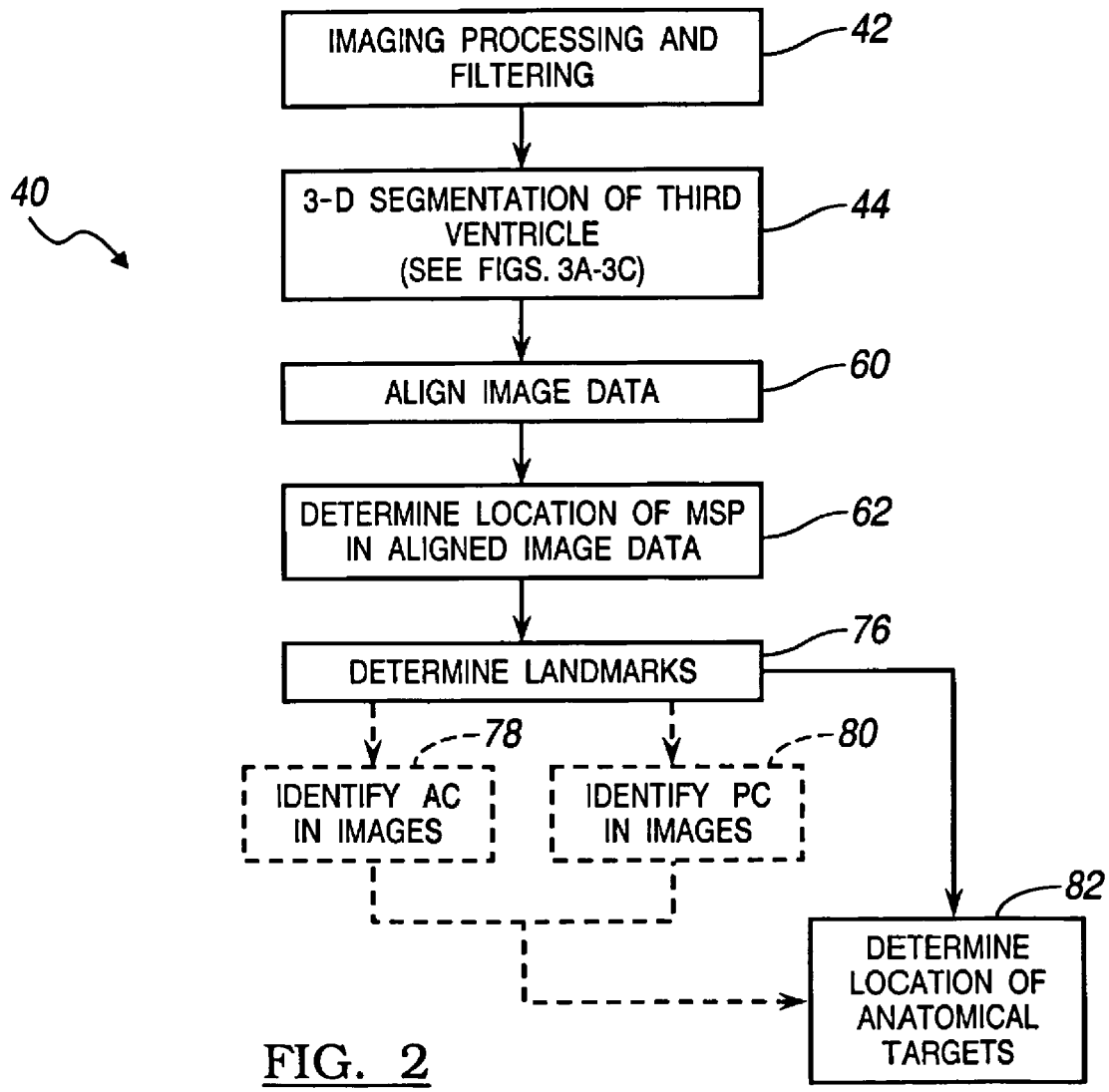
FIG. 2 is a flowchart illustrating in greater detail a method of determining an anatomical landmark.

Continuing reference to FIG. 2 and the determination of targets based on the images (e.g., the pre-processed images) can be used to determine anatomical landmarks in block 76. It will be understood that any appropriate anatomical landmarks may be determined, for example, the identity of the anterior commissure (AC) can be found in the images in block 78 and the identity of the posterior commissure (PC) can be found in the images in block 80. It is understood that determining these particular landmarks, the AC and the PC, are simply examples of the landmarks that can be determined or identified in the images. The AC and the PC can be found for selected procedures in the brain, such as deep brain stimulation.

Identifying the AC can use various techniques. For example, the AC is located in the brain generally immediately inferior of the column of the fornix. The AC is a bundle of nerve fibers that interconnects the two hemispheres of the brain. The bundled nerve fibers that define the AC is generally revealed in the image data as having high gray level intensity values in the image data. Therefore, after identification of the MSP, the AC can be located by finding the highest intensity pixel or pixels that is inferior of the MSP. Generally, the AC landmark is found in the front contour of the third ventricle and on the same level as the brightest pixel or the highest intensity pixel in the image data. It will also be understood that the AC can be found relative to the edge of the determined third ventricle or the edge of the commissure. For example, an edge of the third ventricle can be used to define a location of the commissure and the anterior region thereof can be used to define the AC.

The AC can also be determined or have as a seed point a region that is at an edge of the AC. In the image data the commissure includes high intensity data or bright data, as discussed above. The area adjacent to the commissure, however, generally being the ventricle, can be dark. Thus, an area where the intensity changes can be an edge where the commissure and the ventricle meet. The system 40 can use this as either a starting point to determine the AC in block 78 or can use it as a determined point for the AC, as well. It will be understood that determining the appropriate AC can be performed according to any various embodiments, including those discussed herein.

At any appropriate time, the PC can also be identified from the images in block 80. The PC is also a nerve bundle located in the brain that also crosses the mid-line of the epithalamus just dorsal to the point where the cerebral aqueduct opens into the third ventricle. The PC can be identified by its geometrical location to the cerebral aqueduct in the image data. The cerebral aqueduct can also be determined based upon 3-D segmentation of the image data to provide an additional landmark for the determination of the PC. Various techniques can be used to segment the image data to determine the position of the cerebral aqueduct such as using a histogram based method, for example, the known Otsu's thresholding method. The thresholding method can help separate the object, which appears dark in the image data, and the background, which appears light. The thresholding procedure allows for a determination of a three-dimensional boundary of a particular object. Therefore, the thresholding operation can determine the pixels in the image data that define the boundary of the object, such as the cerebral aqueduct. Once the cerebral aqueduct can be determined, the PC can be determined due to its location relative to the cerebral aqueduct. As discussed above, the PC crosses the midline of the epithalamus just dorsal to the point where the cerebral aqueduct opens into the third ventricle. By determining the cerebral aqueduct relative to the third ventricle, the location of the PC can be determined in block 80.

The PC can also be determined, at least in part, by use of determining an edge of the third ventricle and the commissure, as discussed in relation to the AC. As discussed above the edge between the commissure and the ventricle can be used as the PC or as a starting point to determine the PC. Also, as discussed above the edge can be determined automatically by a processor analyzing the image data, manually by a user, or combinations thereof.

Figure 5:
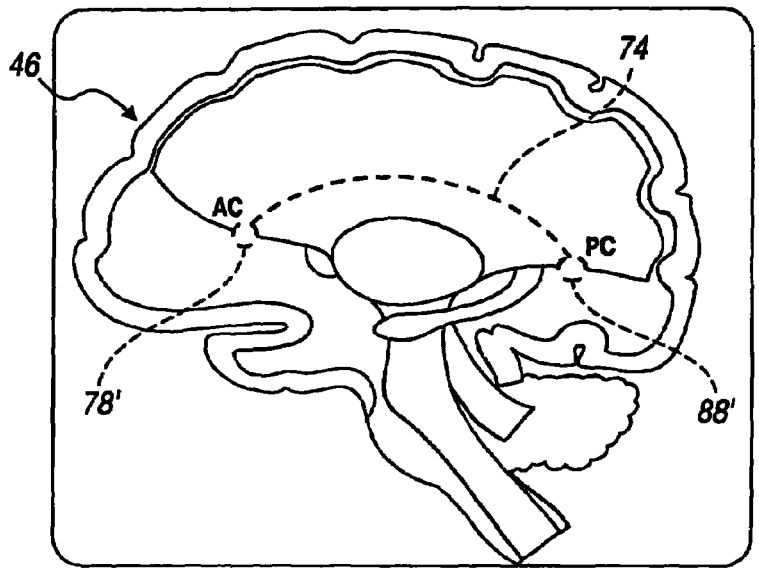
FIG. 5 illustrates a cross-sectional view of image data with identified anatomical landmarks.

With reference to FIG. 5, the image of the brain 46 can be illustrated to show the various portions that are identified therein. For example, the AC can be identified as 78' and the PC can be identified at 88' relative to the MSP 74. The determined anatomical landmarks, as illustrated in FIG. 5, can then be used to determine a location of anatomical targets, as set out in block 24 in the guided procedure 18. The determination of anatomical targets in block 82 can be based upon the determined landmarks. As discussed above, the landmarks can be identified, according to various embodiments of the present teachings, from the image data obtained from a patient. The anatomical targets can include substantially functional targets that are relatively indistinguishable from the surrounding structures. Therefore, the determination of the anatomical targets can be based upon the identified locations of the identifiable anatomical target landmarks and the known anatomical location of the target relative to the landmarks.

The anatomical targets can be any appropriate targets, for example, the sub-thalamic nucleus (STN) discussed above. The STN may be identified for various purposes, such as deep brain stimulation (DBS) thereof. The STN can be determined relative to the anatomical landmarks by finding a point or region a distance relative to the anatomical landmarks in the image data. For example, the STN can be about 3.35 mm posterior, about 12.3 mm lateral, and about 4.9 mm inferior of a point midway between the AC and the PC or the mid-commissural point (MCP). Therefore, a functional target or anatomical target can be determined based upon the identified anatomical landmarks in the image data and selecting a functional target that is positioned in a known region relative to the anatomical landmarks, such as in the brain.

The anatomical target determined in block 82 can also be refined or assisted in determination with an instrument, such as the device 252. For example, an initial or primary target can be found or determined in block 82. An instrument, such as a recorder or sensing device can then be used to assist in refining the exact location or boundaries of the anatomical target found in block 82. In other words, the recorder can be or act as an indication system. The recorder can be used to record or determine activity in various regions of the brain, or any anatomical region, to assist in refining a boundary of the anatomical target in block 82. Thus, one will understand the determination of the anatomical target can be completely automatic, partially automatic (i.e. assisted manually by a user), or any combination thereof.

Figure 6:
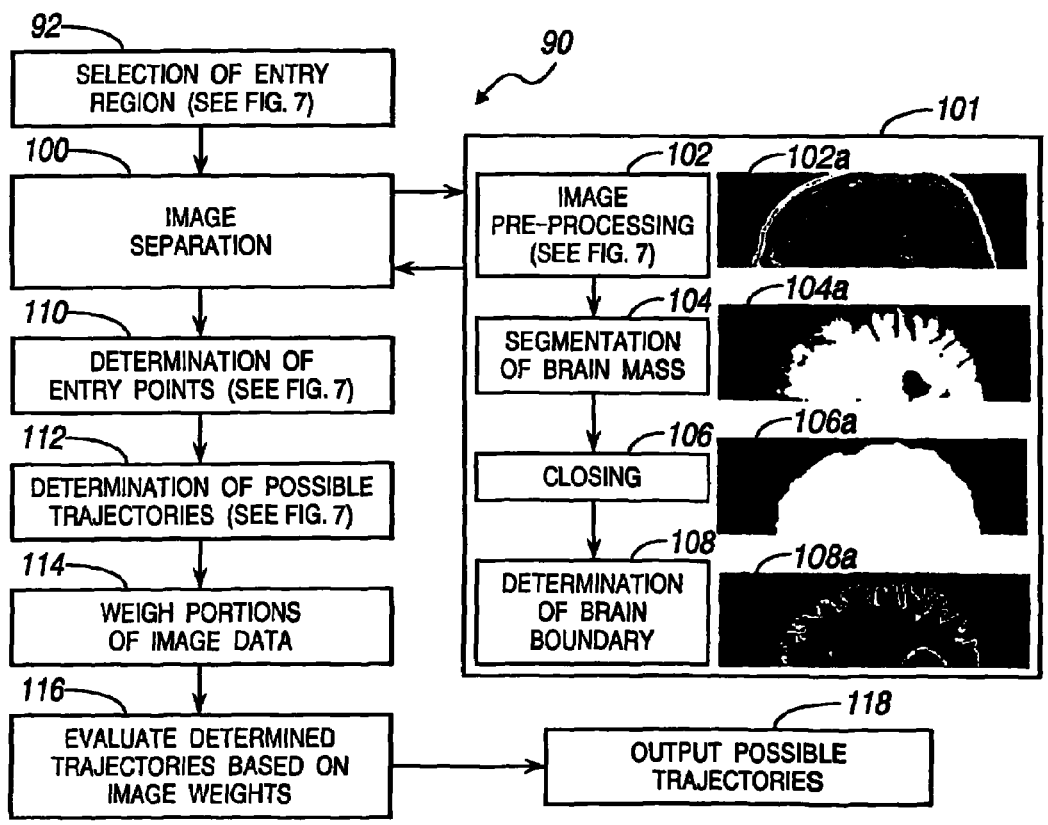
FIG. 6 illustrates a flowchart of a method of determining trajectories to reach an anatomical target.

The determined location of the functional or anatomical target can then be used to determine a selected location for a treatment device, determine a trajectory to reach the anatomical target, or for other purposes as discussed in further detail herein. After the target, such as the anatomical or functional target, has been determined or located, a determination of a trajectory to reach the target can be determined, in block 26 of the guided procedure 18. The determination of an appropriate trajectory to reach the target in block 26, is described in more detail in a trajectory determination method 90 illustrated in a flowchart of FIG. 6.

Figure 7:
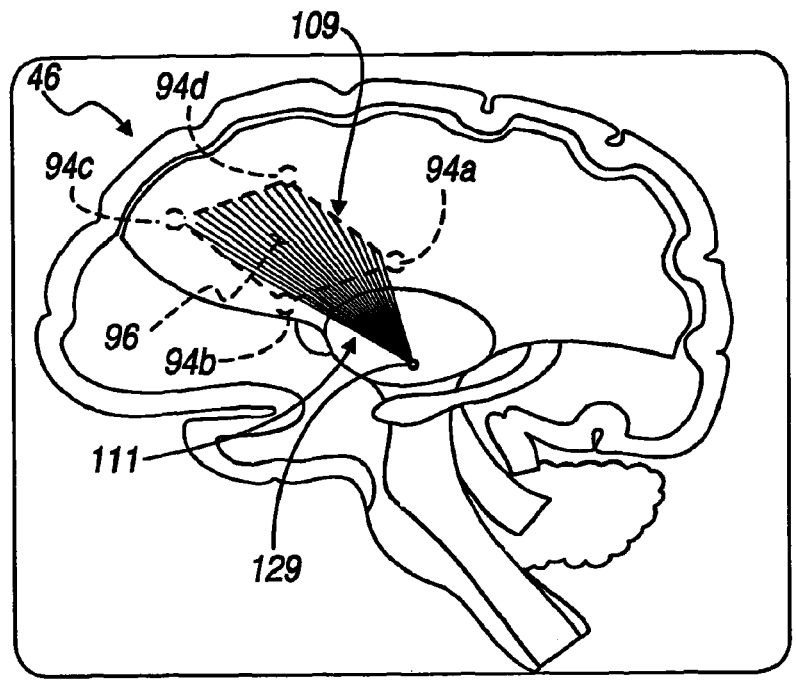
FIG. 7 is an illustration of image data including an entry region.

Initially, a selection of an entry region 96 is performed in block 92. The entry region 96 can be any appropriate region of the anatomy and can include or be generally defined by four vertices. The four vertices can define a two-dimensional region that can be safely used as an entry point for a delivery device, such as a deep brain stimulation probe. With reference to FIG. 7, the four vertices can include 94a, 94b, 94c, and 94d. The region 96 defined by the four vertices 94a-94d can generally be termed the entry region 96. The entry region 96, when performing a procedure on the brain, can define a region of the skull or brain that is selected for safe entry of a probe. The selected entry region 96 can be a region known to one skilled in the art, can be dependent upon patient specific information, or combinations thereof. Nevertheless, the entry region 96 can be selected based upon known anatomy or brain structure to substantially ensure that no critical, dangerous, or selected regions of the brain anatomy will be breached, such as various veins, sulci, and the like. The entry region for a specific procedure, such as deep brain stimulation of the sub-thalamic nucleus, can generally be defined in the anterior region of the skull. Although any appropriate region of the skull can be used as an entry region for an appropriate procedure.

The entry region 96 can be substantially manually determined or substantially automatically determined by a processor. Further, the entry region 96 can be based upon patient specific information, such as the image data, generally accepted anatomy, or a combinations thereof. The entry region 96 can also be determined based upon a computation of automatic and manual determinations. For example, if the patient had a prior procedure performed in a similar area, the method and system can take this into consideration to select an entry region 96 away from this area. The entry region 96 can be determined based upon many factors, such as generally accepted region of the skull or brain that is safe for entry of an instrument, patient specific information that is based upon prior procedures and particular specific anatomy of the selected patient, or other appropriate information. For example, when attempting to perform DBS on the STN in the brain a region slightly anterior on the skull is generally understood to be acceptable for entry of a probe to access the STN. It will be understood, however, that any appropriate region of the skull can be used to access a selected region of the brain. Therefore, this region can be provided as the entry region 96 for the process 90 to determine selected trajectories.

Selection of an entry region or point (block 110) can also be dependant upon the image data obtained and analyzed. For example, after the landmarks are found in block 76 or the anatomical target is determined in block 82 a proposed entry point or region can be determined based upon the location of the specific target. Thus, although a generally accepted region or entry point can be used in the process 90 to determine a trajectory, a proposed or determined entry point or region based on patient specific information, such as image data, can also be used.

Once the selection of an entry region in block 92 has been determined, the image data can be further processed or separated in block 100. The image separation process 100 can be any appropriate process, and may be specifically referred to as brain separation when performing a brain specific procedure. Generally, the image separation will allow for a determination of boundaries of specific portions of the anatomy, such as the boundary of the brain, to assist in determining an appropriate trajectory to reach the anatomical targets.

The image separation in block 100 can include a subroutine 101 that can include various steps. A first step in the subroutine 101 can include image pre-processing in block 102, such as filtering and smoothing of the image data and illustrated in block 102a. The image pre-processing can include any appropriate system or methods, including the schemes described above. The image pre-processing can allow for better processing of the image data later by removing unneeded or unwanted data and smoothing the data that is remaining for simplified processing. The subroutine 101 can also include segmentation of the brain's mass in block 104. Segmentation of the brain mass can include segmenting the region of the image data substantially defining the brain and removing unnecessary data, such as the skull, the optic nerves, and other portions not relevant to selected brain structures, such as the anatomical targets, thus this can clarify the image data. The segmentation of the brain mass in block 104 can assist in allowing the image data to be separated just to the area of the anatomy to be operated on. It will be understood, however, that any appropriate region could be segmented and segmenting the brain mass is merely exemplary for performing a brain specific procedure. Closing in block 106 and illustrated in block 106a can then also be performed on the image data for removing holes and crevices in the segmented brain mass to determine a volume which bounds and fully contains the brain mass. In other words, closing can be used to fill in an area or volume within a bound. Finally, the calculation of the outer brain boundary can be determined in block 108 and illustrated in block 108a. Again, it will be understood that any appropriate boundary can be determined and determining an outer brain boundary is merely exemplary for performing a brain specific procedure. Nevertheless, the brain boundary can assist in determining various regions of the brain that can be avoided or are desirable to be avoided in a specific procedure. The image separation subroutine 101 can then provide a separated image to the image separation block 100.

After the image has been separated in block 100, determination of all possible entry points 109 (FIG. 7) can be performed in block 110. The determination of all entry points 109 in block 110 can be based upon the entry region 96 (FIG. 7) selected in block 92 and the determination of the location of the anatomical target 129 in block 24. The entry points 109 determined in block 110 can be any possible entry point that would allow access to the anatomical target 129 determined in block 24. It will be understood that the determined entry points 109 can be based upon a selected structure or limitation of a delivery device. For example, the determination of entry points 109 in block 110 can be based upon all possible trajectories that will allow for a straight line access to the anatomical target. It will be understood that the entry points may be augmented or different based upon the ability to move a probe in a non-linear or leveled manner or other characteristics, including, but not limited to size, shape, or rigidity.

Determination of all possible trajectories 111 (FIG. 7) from the determination of entry points in block 110 to the anatomical target 129 can be performed in block 112. The determination of the possible trajectories 111 can be based upon a selected path or possible path of an instrument, such as a deep brain stimulation probe. It will be understood that trajectories can be straight line, curved, or combinations thereof and can be based upon the characteristics of the selected instruments. For example, various steerable probes or catheters may be used. Steerable catheters can be steered by magnetic fields, mechanical mechanisms, or other appropriate methods of mechanisms. The possible trajectories can be any possible trajectories 11 from all of the determined entry points 109 in block 110 to the determined anatomical target 129. The determination of possible trajectories in block 112 can be all possible trajectories or trajectories based upon selected characteristics, such as desired angles, time of calculation, and the like. Generally, determination of trajectories in block 112 can be based simply on geometrical characteristics between the entry points and the anatomical targets. It will be understood that the determination of possible trajectories in block 112 can be performed in several selected manners. For example, as discussed herein, the image data can be weighted and the image data can therefore include certain regions through which an instrument can be passed and certain regions through which an instrument cannot be passed. Therefore, the determination of trajectories can initially take into account the weighted image data. Alternatively, the possible trajectories can include all possible trajectories that allow a selected instrument, such as a substantially straighter linear probe, to pass through each of the entry points in the entry region 96 and reach the anatomical target determined in block 24. It will be understood that each of these possible trajectories may include an angle, a distance, and the like, as illustrated in FIG. 7. Therefore, the determination of trajectories can include the determination of all possible trajectories, the initial determination of all possible trajectories that achieve a selected result (e.g., not passing through a selected region of the brain), or other selected characteristics. Nevertheless, the possible trajectories determined in block 112 can be further evaluated in block 116, as discussed further herein.

The image data can be weighted in block 114. The weighting of the image data can be performed at any time, but can generally weight the image data based upon various characteristics of the image data. For example, the various portions of the image data, such as pixels or voxels, can be weighted based upon portions of the anatomy that are to be avoided or portions of the anatomy that are harmless if passed through by an instrument. For example, various portions, such as pixels of the image data, can be weighted based upon the indication that the pixel is part of a vein (i.e., shows as a bright white or bright grey area), not a sulcus of the brain, not in a area that is filled with fluid, (i.e., shows dark or has a low intensity pixel in the image data). The pixels that include the greatest contrast can be weighted higher while pixels with a lower contrast can be weighted lower for determining an appropriate trajectory or for a valid weighting the trajectories in block 116.

Different schemes can be used to weighting the image data. For example, the system can weight the image data so that no trajectory is acceptable if it passes through a vessel, a sulcus, or an area filled with fluid. Certain areas that are weighted in the image data in block 114 can be weighted in such a manner that the pixel area can absolutely not be traversed by a trajectory or can simply be weighted as better or worse than other pixels. The schemes may also allow for a determination of a better trajectory than another based upon the overall weight of the pixels traversed, the type of pixels traversed, etc.

The evaluation of the determined trajectories in block 116 can be based on the image weighting in block 114, such as the weighting of the pixels, to evaluate the appropriateness of the determined trajectories from block 112. The evaluation of the determined trajectories can be used to evaluate whether a specific trajectory, which was determined in block 112, will meet certain requirements that can be a part of the weighting process in block 114. Any trajectory that meets a threshold can be further evaluated based upon a comparison of a single one of the trajectories from block 112 to any of the other determined trajectories from block 112. Once the evaluation of the determined trajectories is performed in block 116, an output of the possible trajectories is performed in block 118.

The output of possible trajectories in block 118 can include trajectories that meet various criteria, such as not breaching certain weighted portions of the image data, or including a certain threshold based upon, or when compared to, the other trajectories. The output of possible trajectories in block 118 can include all trajectories and can also include an appropriateness or optimization value. The appropriateness value can be based on a formula for grading each of the possible trajectories. Also, the output trajectories can include only a selected number of trajectories based upon the best or optimized or a certain number of optimized trajectories. The best trajectories can be those that are optimized or those that have minimized a selected affect on a region of the anatomy, such as the brain. One skilled in the art will understand that one or more plan or trajectory may have the same optimal affect on the selected region of the anatomy.

Figure 8:
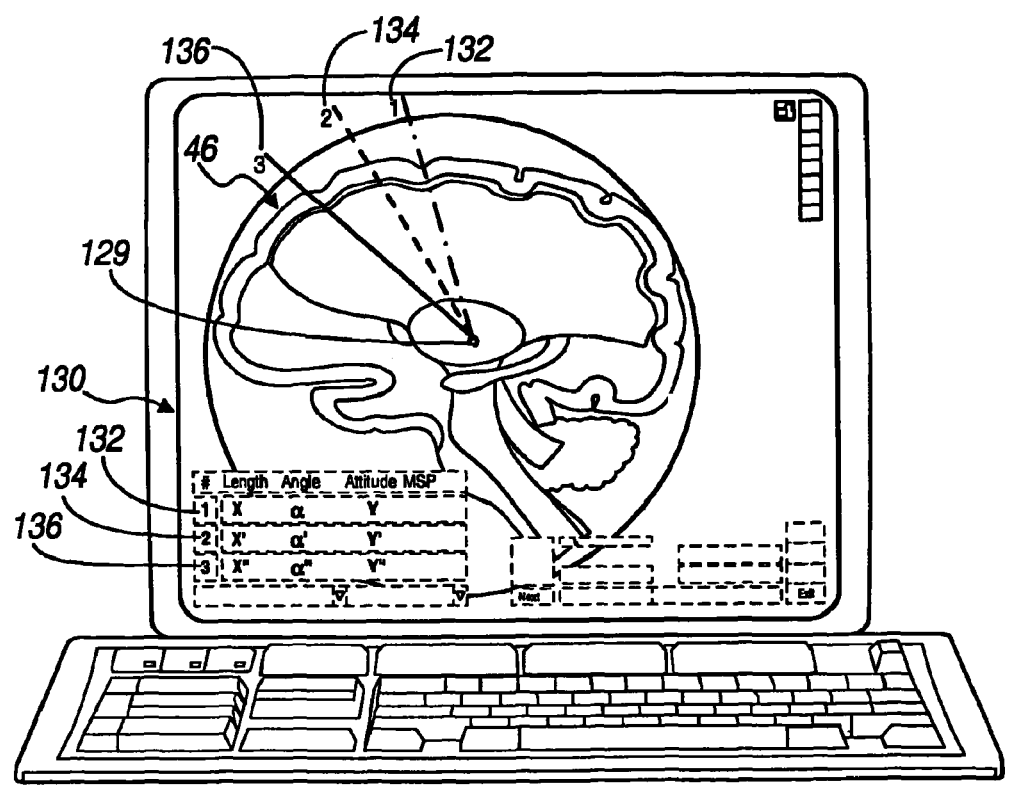
FIG. 8 illustrates a system, including image data and outputs of selected trajectories.

With reference to FIG. 8, the output of possible trajectories can be any appropriate output, such as a human readable display 130. The human readable display 130 can include a monitor that is driven by video graphics portion of a system. On the display 130, the selected image data, such as an exemplary image data 46, is displayed. Further, an appropriate number of determined trajectories can be displayed such as trajectories 132, 134, and 136. The trajectories can also include various data related to the trajectories 132-136 including the length, an angle to a selected axis, a distance from the MSP, or various other data. The output of possible trajectories displayed on the display 130 can then be used by a user, such as a physician, to determine an appropriate trajectory or to select a trajectory. Therefore, a user can make the final determination of the appropriate trajectory that is output in block 118.

It will be understood that the guided procedure 18, including determination of the anatomical targets in block 24 and the determination of trajectories in block 26 can be performed substantially automatically (e.g., with a processor performing various instructions of an algorithm), manually, or combinations thereof. For example, a processor (FIG. 9, reference numerals 224a or 226) can include or be provided with a set of instructions that, when executed, will perform the steps described in method 18, including the detailed steps in 40 and 90, to determine the appropriate anatomical targets and the appropriate trajectories to reach the targets. The processor system, described in more detail herein, can also then output the appropriate trajectories for selection by a user. The system can also be augmented by a user, where the user may perform parts of the methods or provide the seed data for various portions of the method such as seeding the pixels or voxels for the segmentation. Nevertheless, the processor 224, 226 executing the instructions can include a Pentium IV 1.6 GHz processor that can generally determine the anatomical targets from T1 MRI image data in about 15-30 seconds. The image data, the instructions, and other appropriate portions can be stored on any appropriate memory structure 91 or mechanism such as a hard disk, flash memory, system RAM, or removable storage media. The memory structure can be associated with the planning processor 226, the work station 244, or any appropriate portion. The system can thus allow a user to substantially standardize a procedure and reduce time of determining the various anatomical landmarks by providing analysis of the image data by the processor system. It will be understood that the various portions of the method can be described in algorithms to determine the segmentation of the data, the various trajectories, and the like.

Once the determination trajectory has been performed in block 26, a determination of a method for performing the procedure can be performed in block 28. As discussed above, various types of procedures can include a frameless guided procedure in block 30, a stereotactic frame procedure in block 32, or a substantially open procedure block 34. It will also be understood that different procedures can be combined in an appropriate manner to achieve a selected result. For example, a computer assisted surgery system or a navigation system can include navigated instruments, a localizer or array, a dynamic reference frame, and other appropriate portions.

Figure 9:
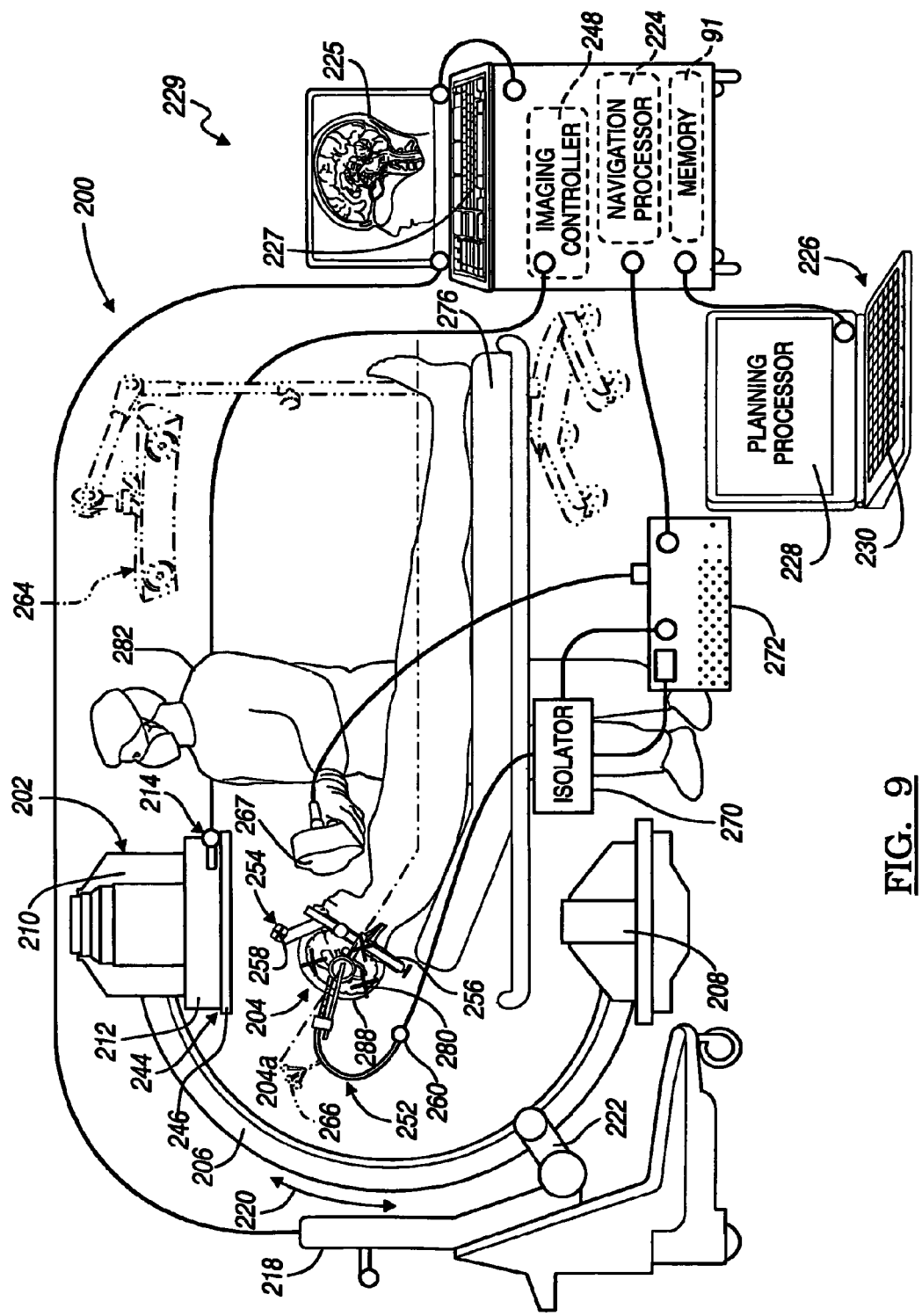
FIG. 9 illustrates a diagram of a surgical navigation system according to various embodiments.

An exemplary system that can be used to automatically or substantially automatically perform at least portions of the guided procedure is diagrammatically illustrated as an image-guided navigation system 200, in FIG. 9, that can be used for various procedures with the guided procedure 18. The navigation system 200, including the navigation processor 224 and a planning processor 226 can execute instructions to perform at least portions of the guided procedure 18. The navigation system 200 can also be used to track the location of a device relative to a patient 204 to assist in the implementation of the guided procedure 18.

It should further be noted that the navigation system 200 may be used to navigate or track devices including: catheters, probes, needles, guidewires, instruments, implants, deep brain stimulators, electrical leads, etc. Moreover, the device can be used in any region of the body. The navigation system 200 and various devices may be used in any appropriate procedure, such as one that is generally minimally invasive, arthroscopic, percutaneous, stereotactic, or an open procedure. Although an exemplary navigation system 200 can include an imaging device 202. One skilled in the art will understand that the discussion of the imaging device 202 is merely for clarity of the present discussion and any appropriate imaging system, navigation system, patient specific data, and non-patient specific data can be used.

The navigation system 200 can include the optional imaging device 202 that is used to acquire pre-, intra-, or post-operative or real-time image data of a patient 204. The image data acquired with the imaging device 204 can be used by the procedure 18 to assist in determining the anatomical targets and the trajectories. The illustrated imaging device 202 can be, for example, a fluoroscopic x-ray imaging device that may be configured as a C-arm 206 having an x-ray source 208, an x-ray receiving section 210, an optional calibration and tracking target 212 and optional radiation sensors 214. Image data may also be acquired using other imaging devices, such as those discussed above and herein. An example of a fluoroscopic C-arm x-ray device that may be used as the optional imaging device 202 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

The calibration and tracking target 212 can include calibration markers (not illustrated) to calibrate the imaging system 262 as is generally known. An optional imaging device controller 218 may control the imaging device 202, such as the C-arm 206, can capture the x-ray images received at the receiving section 210 and store the images for later use. The controller 218 may also be separate from the C-arm 206 and/or control the rotation of the C-arm 206. For example, the C-arm 206 can move in the direction of arrow 220 or rotate about a longitudinal axis 204a of the patient 204, allowing anterior or lateral views of the patient 204 to be imaged. Each of these movements involves rotation about a mechanical axis 222 of the C-arm 206.

In operation, the C-arm 206 generates x-rays from the x-ray source 208 that propagate through the patient 204 and calibration and/or tracking target 212, into the x-ray receiving section 210. It will be understood that the tracking target need not include a calibration portion. The receiving section 210 generates image data representing the intensities of the received x-rays. Typically, the receiving section 210 includes an image intensifier that first converts the x-rays to visible light and a charge coupled device (CCD) video camera that converts the visible light into digital image data. Receiving section 210 may also be a digital device that converts x-rays directly to digital image data for forming images, thus potentially avoiding distortion introduced by first converting to visible light. With this type of digital C-arm, which is generally a flat panel device, the optional calibration and/or tracking target 212 and the calibration process discussed below may be eliminated. Also, the calibration process may be eliminated or not used at all for various procedures. Alternatively, the imaging device 202 may only take a single image with the calibration and tracking target 212 in place. Thereafter, the calibration and tracking target 212 may be removed from the line-of-sight of the imaging device 202.

Two dimensional fluoroscopic images that may be taken by the imaging device 202 are captured and stored in the C-arm controller 218. Multiple two-dimensional images taken by the imaging device 202 may also be captured and assembled to provide a larger view or image of a whole region of a patient, as opposed to being directed to only a portion of a region of the patient. For example, multiple image data of a patient's head may be appended together to provide a full view or complete set of image data of the head that can be later used. The multiple images, such as multiple 2D images, can be stitched together to form a larger view in 2D or can be reconstructed to create a 3D dataset of a volume. Other imaging techniques such as T1 or T2 weighted MRI can be used to accumulate multiple slices of a patient's head to form a three-dimensional model at the patient's head and brain to determine location of anatomical targets.

The image data can then be forwarded from the C-arm controller 218 to a navigation computer and/or processor 224 having a display 225 and a user interface 227. The navigation processor 224, display 225, and user input interface 227 can be part of a work station 229. The navigation processor 224 can include a planning processor, as discussed herein, or a separate planning processor system 226 can be included. The planning processor system 226 can also include a display 228 and a user input 230. It will also be understood that the image data is not necessarily first retained in the controller 218, but may be directly transmitted to the workstation 229 or the planning processor system 226.

The work station 229 or optimization processor 228 provides facilities for displaying the image data as an image on the displays 226 or 228, saving, digitally manipulating, or printing a hard copy image of the received image data. The user interface 230, which may be a keyboard, mouse, touch pen, touch screen or other suitable device, allows a physician or user to provide inputs to control the imaging device 202, via the C-arm controller 218, or adjust the display settings of the display 225.

When the x-ray source 208 generates the x-rays that propagate to the x-ray receiving section 210, the radiation sensors 214 sense the presence of radiation, which is forwarded to the C-arm controller 218, to identify whether or not the imaging device 202 is actively imaging. This information is also transmitted to a coil array controller 232, further discussed herein, .that can be a part of the workstation 229. For example, the array controller 232 can be controlled by the navigation processor 224. Alternatively, a person or physician may manually indicate when the imaging device 202 is actively imaging or this function can be built into the x-ray source 208, x-ray receiving section 210, or the control computer 218.

While the optional imaging device 202 is shown in FIG. 9, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative CT, single photo emission computed tomography (SPECT), or planar gamma scintigraphy (PGS) may also be used to acquire 2D, 3D or 4D pre- or post-operative and/or real-time images or image data of the patient 204. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference.

Figure 10:
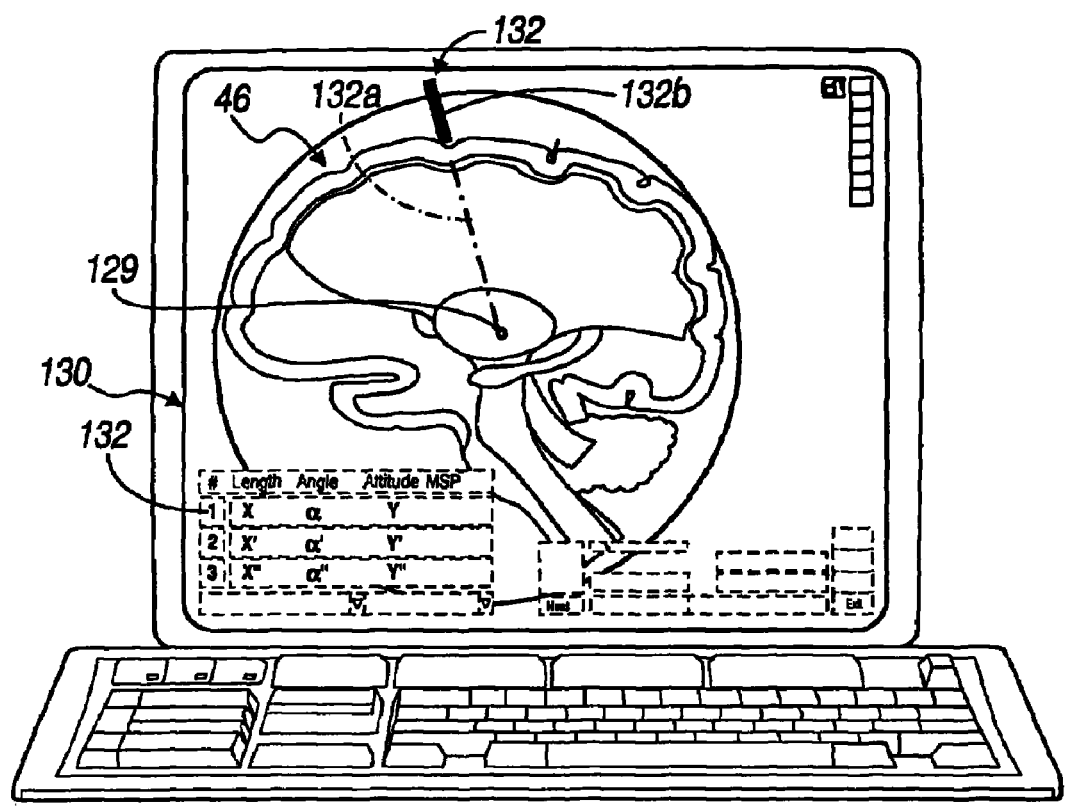
FIG. 10 is a detailed view of the display 130 displaying an icon that is exemplary superimposed on image data.

Image datasets from hybrid modalities, such as positron emission tomography (PET) combined with CT, or single photon emission computer tomography (SPECT) combined with CT, can also provide functional image data superimposed onto anatomical data to be used to confidently reach target sites within the patient 204. It should further be noted that the optional imaging device 202, as shown in FIG. 10, provides a virtual bi-plane image using a single-head C-arm fluoroscope as the optional imaging device 202 by simply rotating the C-arm 206 about at least two planes, which could be orthogonal planes to generate two-dimensional images that can be converted to three-dimensional volumetric images. By acquiring images in more than one plane, an icon representing the location of an impactor, stylet, reamer driver, taps, drill, deep brain stimulators, electrical leads, needles, implants, probes, or other instrument, introduced and advanced in the patient 204, may be superimposed in more than one view on display 225 or 228 allowing simulated bi-plane or even multi-plane views, including two and three-dimensional views.

These types of imaging modalities may provide certain distinct benefits for their use. For example, magnetic resonance imaging (MRI) is generally performed pre-operatively using a non-ionizing field. This type of imaging provides very good tissue visualization in three-dimensional form and also provides anatomy and functional information from the imaging. MRI imaging data is generally registered and compensated for motion correction using dynamic reference frames (DRF) discussed further herein. Also, different types of MRI techniques can be used to more clearly illustrate different portions of the anatomy. As discussed above, T1 weighted MRI images may be used to display selected anatomical regions in the brain.

With continuing reference to FIG. 9, the navigation system 200 can further include an electromagnetic navigation or tracking system 244 that includes a localizer, such as a transmitter coil array 246, a coil array controller 248, a navigation probe interface 272, a device 252 (e.g. catheter, needle, or instruments, as discussed herein) and a dynamic reference frame 254. The dynamic reference frame 254 can include a dynamic reference frame member or holder 256 and a removable tracking sensor 258. Alternatively, the dynamic reference frame 254 can include a tracking sensor that is formed integrally with the dynamic reference frame member 256. One skilled in the art will understand that the tracking sensor 258 can be any appropriate device that can be an emitter, a receiver, a reflector, a sensor to sense a field, or any other appropriate device that can be tracked by a tracking system including a localizer.

The device 252 can be any appropriate device, for example and referred to herein as a catheter. Other appropriate devices can be used to delivery a therapy to a region of the anatomy or to record information from a region of the anatomy. For example, a recording device can be placed in the cranium of the patient 204 to record electrical activity of a selected region of the brain for analysis and treatment options. Thus, it will be understood that the device 252 can be selected to be any appropriate device, and a stimulator, catheter, probe, etc. are merely exemplary.

The transmitter coil array 246 may also be supplemented or replaced with a mobile localizer 267. The mobile localizer 267 may be one such as that described in U.S. patent application Ser. No. 10/941,782, filed Sep. 15, 2004, now U.S. Pat. App. Pub. No. 2005/0085720, and entitled "METHOD AND APPARATUS FOR SURGICAL NAVIGATION", herein incorporated by reference. As is understood the localizer array can transmit signals that are received by the dynamic reference frame 254, and a tracking sensors 260. The dynamic reference frame 254 and the tracking sensors 260 can then transmit signals based upon the received signals from the array.

It will be understood that the tracking system may be any appropriate tracking system and can include an optical tracking system with an optical localizer 264, illustrated in phantom. Optical tracking systems can include the StealthStation® TRIA™ and StimPilot™, and electromagnetic systems can include the AxiEM™, all sold by Medtronic Navigation of Louisville, Colo. Other tracking systems include acoustic, radiation, radar, infrared, laser, accelerometer, etc. The optical localizer 264 can transmit and receive, or combinations thereof. An optical tracking sensor 266 can be interconnected with the device 252, or other portions such as the dynamic reference frame 254. As is generally known the tracking sensor 266 can reflect or transmit an optical signal to the optical localizer 264 that can be used in the navigation system 200 to navigate or track various elements.

Further included in the navigation system 200 may be an isolator circuit or assembly 270. The isolator assembly 270 may be included in a transmission line to interrupt a line carrying a signal or a voltage to a navigation device interface 272. Alternatively, the isolator circuit included in the isolator assembly 270 may be included in the navigation device interface 272, the device 252, the dynamic reference frame 254, the transmission lines coupling the devices, or any other appropriate location. The isolator assembly 270 is operable to isolate the patient from any of the instruments or portions that are in contact with the patient 204 should an undesirable electrical surge or voltage take place.

It should further be noted that the entire tracking system 244 or parts of the tracking system 244 may be incorporated into the imaging device 202, including the work station 229 and radiation sensors 214. Incorporating the tracking system 244 may provide an integrated imaging and tracking system. Any combination of these components may also be incorporated into the imaging system 202, which can include an appropriate imaging device.

The transmitter coil array 266 is shown attached to the receiving section 210 of the C-arm 206. It should be noted, however, that the transmitter coil array 266 may also be positioned at any other location as well. For example, the transmitter coil array 266 may be positioned at the x-ray source 208, within or atop an operating room (OR) table 276 positioned below the patient 204, on siderails associated with the OR table 276, or positioned on the patient 204 in proximity to the region being navigated, such as on the patient's chest. The coil array is used in an electromagnet tracking system as the localizer therefore. It is understood by one skilled in the art that any appropriate localizer may be used. The transmitter coil array 266 may also be positioned in the items being navigated, further discussed herein. The transmitter coil array 266 can include a plurality of coils that are each operable to generate distinct electromagnetic fields into the navigation region of the patient 204, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 266 is controlled or driven by the coil array controller 232. The coil array controller 232 drives each coil in the transmitter coil array 266 in a time division multiplex or a frequency division multiplex manner. In this regard, each coil may be driven separately at a distinct time or all of the coils may be driven simultaneously with each being driven by a different frequency. Upon driving the coils in the transmitter coil array 266 with the coil array controller 232, electromagnetic fields are generated within the patient 204 in the area where the medical procedure is being performed, which is again sometimes referred to as patient space. The electromagnetic fields generated in the patient space induce currents in a sensor 258 positioned on or in the device 252. These induced signals from the device 252 are delivered to the navigation device interface 272 through the isolation assembly 270 and subsequently forwarded to the coil array controller 232. The navigation device interface 272 may provide all the necessary electrical isolation for the navigation system 200. Alternatively, the electrical isolation may also be provided in the isolator assembly 270. Nevertheless, the isolator assembly 270 may be included in the navigation device interface 272 or may be integrated into the device 252, and any other appropriate location. The navigation device interface 272 can also include amplifiers, filters and buffers to directly interface with the sensors 258 in the device 252. Alternatively, the device 252, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation device interface 272.

When the navigation system 200 uses an EM based tracking system, various portions of the navigation system 200, such as the device 252, the dynamic reference frame (DRF) 254, the device 252, are equipped with at least one, and generally multiple, EM tracking sensors 260, that may also be referred to as localization sensors. The EM tracking sensor 260 can include one or more coils that are operable with the EM localizer array 266 or 267. An alternative sensor may include an optical sensor, such as the optical sensor 258a, and may be used in addition to or in place of the electromagnetic sensor 258. The optical sensor may work with the optional optical localizer 264. One skilled in the art will understand, however, that any appropriate tracking sensor can be used in the navigation system 200. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The EM tracking sensor. 258 on the device 252 can be in a handle or inserter that interconnects with an attachment and may assist in placing an implant or in driving a portion. The device 252 can include a graspable or manipulable portion at a proximal end and the tracking sensor 258 may be fixed near the manipulable portion of the device 252 or at a distal working end, as discussed herein. The tracking sensor 258 can include an electromagnetic sensor to sense the electromagnetic field generated by the transmitter coil array 266 that can induce a current in the electromagnetic sensor 258.

The dynamic reference frame 254 of the tracking system 244 is also coupled to the navigation device interface 272 to forward the information to the coil array controller 232. The dynamic reference frame 254, according to various embodiments, may include a small magnetic field detector. The dynamic reference frame 254 may be fixed to the patient 204 adjacent to the region being navigated so that any movement of the patient 204 is detected as relative motion between the transmitter coil array 266 and the dynamic reference frame 254. The dynamic reference frame 254 can be interconnected with the patient in any appropriate manner, including those discussed herein. This relative motion is forwarded to the coil array controller 232, which updates registration correlation and maintains accurate navigation, further discussed herein. The dynamic reference frame 254 may be any appropriate tracking sensor used as the dynamic reference frame 254 in the navigation system 200. Therefore the dynamic reference frame 254 may also be optical, acoustic, etc. If the dynamic reference frame 254 is electromagnetic it can be configured as a pair of orthogonally oriented coils, each having the same center or may be configured in any other non-coaxial or co-axial coil configurations.

The dynamic reference frame 254 may be affixed externally to the patient 204, adjacent to the region of navigation, such as on the patient's cranium, etc., as shown in FIG. 9. The dynamic reference frame 254 can be affixed to the patient's skin, by way of a selected adhesive patch and/or a tensioning system. The dynamic reference frame 254 may also be removably attachable to a fiducial marker 280. The fiducial markers can be anatomical landmarks or members attached or positioned on the patient's 204 body. The dynamic reference frame 254 can also be connected to a bone portion of the anatomy. The bone portion can be adjacent, the area of the procedure, the bone of the procedure, or any appropriate bone portion.

Briefly, the navigation system 200 operates as follows. The navigation system 200 creates a translation map between all points in the image data or image space and the corresponding points in the patient's anatomy in patient space. After this map is established, the image space and patient space are registered. In other words, registration is the process of determining how to correlate a position in image space with a corresponding point in real or patient space. This can also be used to illustrate a position of the device relative to the proposed trajectory and/or the determined anatomical target. The work station. 229 in combination with the coil array controller 232 and the C-arm controller 218 identify the corresponding point on the pre-acquired image or atlas model relative to the tracked device 252 and display the position on display 225. This identification is known as navigation or localization. An icon representing the localized point or instruments is shown on the display 225 within several two-dimensional image planes, as well as on three and four dimensional images and models.

To register the patient 204, a physician or user 282 may use point registration by selecting and storing particular points from the pre-acquired images and then touching the corresponding points on the patient's anatomy with a pointer probe or any appropriate tracked device, such as the device 252. The navigation system 200 analyzes the relationship between the two sets of points that are selected and computes a match, which allows for a determination of a correlation of every point in the image data or image space with its corresponding point on the patient's anatomy or the patient space.

The points that are selected to perform registration or form a translation map are the fiducial markers 280, such as anatomical or artificial landmarks. Again, the fiducial markers 280 are identifiable on the images and identifiable and accessible on the patient 204. The fiducial markers 280 can be artificial landmarks that are positioned on the patient 204 or anatomical landmarks that can be easily identified in the image data. The artificial fiducial markers 280, can also form part of the dynamic reference frame 254, such as those disclosed in U.S. Pat. No. 6,381,485, entitled "Registration of Human Anatomy Integrated for Electromagnetic Localization," issued Apr. 30, 2002, herein incorporated by reference. It will be understood that the "X" illustrated in FIG. 9 can merely indicate a position of a fiducial marker 280 rather than being the fiducial marker 280.

The system 200 may also perform registration using anatomic surface information or path information as is known in the art (and may be referred to as auto-registration). The system 200 may also perform 2D to 3D registration by utilizing the acquired 2D images to register 3D volume images by use of contour algorithms, point algorithms or density comparison algorithms, as is known in the art. An exemplary 2D to 3D registration procedure, is set forth in U.S. Ser. No. 10/644,680, filed on Aug. 20, 2003, now U.S. Pat. App. Pub. No. 2004-0215071, entitled "Method and Apparatus for Performing 2D to 3D Registration", hereby incorporated by reference.

In order to maintain registration accuracy, the navigation system 200 continuously can track the position of the patient 204 during registration and navigation with the dynamic reference frame 254. This is because the patient 204, dynamic reference frame 254, and transmitter coil array 266 may all move during the procedure, even when this movement is not desired. Alternatively the patient 204 may be held immobile once the registration has occurred, such as with a head frame. Therefore, if the navigation system 200 did not track the position of the patient 204 or area of the anatomy, any patient movement after image acquisition would result in inaccurate navigation within that image. The dynamic reference frame 254 allows the tracking system 244 to track the anatomy and can assist in registration. Because the dynamic reference frame 254 is rigidly fixed to the patient 204, any movement of the anatomy or the transmitter coil array 266 is detected as the relative motion between the transmitter coil array 266 and the dynamic reference frame 254. This relative motion is communicated to the coil array controller 232, via the navigation probe interface 272, which updates the registration correlation to thereby maintain accurate navigation.

The dynamic reference frame 254 can be affixed to any appropriate portion of the patient 204, and can be used to register the patient to the image data, as discussed above. For example, when a procedure is being performed relative to a cranium 288, the dynamic reference frame 254 can be interconnected with the cranium 288. The dynamic reference frame 254 can be interconnected with the cranium 288 in any appropriate manner, such as those discussed herein according to various embodiments.

To enable navigation, registration must be had and the navigation system 200 must be able to detect both the position of the patient's anatomy and the position of the device 252 or attachment member (e.g. tracking sensor 258) attached to the device 252. Knowing the location of these two items allows the navigation system 200 to compute and display the position of the device 252 or any portion thereof in relation to the patient 204. The tracking system 244 is employed to track the device 252 and the anatomy simultaneously.

The tracking system 244, if it is using an electromagnetic tracking assembly, essentially works by positioning the transmitter coil array 266 adjacent to the patient space to generate a low-energy magnetic field generally referred to as a navigation field. Because every point in the navigation field or patient space is associated with a unique field strength, the electromagnetic tracking system 244 can determine the position of the device 252 by measuring the field strength at the tracking sensor 258 location. The dynamic reference frame 254 is fixed to the patient 204 to identify the location of the patient in the navigation field. The electromagnetic tracking system 244 continuously recomputes the relative position of the dynamic reference frame 254 and the device 252 during localization and relates this spatial information to patient registration data to enable image guidance of the device 252 within and/or relative to the patient 204.

To obtain a maximum reference it can be selected to fix the dynamic reference frame 254 in each of at least 6 degrees of freedom. Thus, the dynamic reference frame 254 or any of the tracking sensors 258 can be fixed relative to axial motion X, translational motion Y, rotational motion Z, yaw, pitch, and roll relative to the portion of the patient 204 to which it is attached. Any appropriate coordinate system can be used to describe the various degrees of freedom. Fixing the dynamic reference frame relative to the patient 204 in this manner can assist in maintaining maximum accuracy of the navigation system 200.

In addition the dynamic reference frame 254 can be affixed to the patient in such a manner that the tracking sensor portion thereof is immovable relative to the area of interest, such as the cranium 288. A head band may form a part of the dynamic reference frame 254. Further, a stereotactic frame, as generally known in the art, can be attached to the head band. Such systems for tracking and performing procedures are disclosed in U.S. patent application Ser. No. 10/651,267, filed on Aug. 28, 2003, now U.S. Pat. App. Pub. 2005/0049486, and incorporated herein by reference.

Although the navigation system 244, discussed above, can be provided in a plurality of ways and with a plurality of mechanisms it can be used to track the device 252. As discussed above the device can be a catheter 252 and can be any appropriate catheter and can include a tracking sensor such as the tracking sensor 258. Briefly, it will be understood that the catheter 252 can represent any appropriate instrument such as a deep brain stimulator, a needle, a probe, a guidewire, etc. The tracking sensor 258 included in the catheter 252 can be any appropriate tracking sensor and can be formed in any appropriate manner such as the catheters described in pending U.S. patent application Ser. No. 11/241,837, filed on Sep. 30, 2005, now U.S. Pat. App. Pub. No. 2006/0084867, incorporated herein by reference. The catheter 252 can include the tracking sensors 258 at any appropriate position, such as near a distal end of the catheter 252. By positioning the tracking sensors 258 near the distal end of the catheter 252 knowing or determining a precise location of the distal end can be easily done. Determining a position of the distal end of the catheter 252 can be used to achieve various results, such as determining a precise position of the distal end of the catheter 252, a precise movement of the distal end of the catheter 252, or other appropriate purposes. It will be understood that knowing a position and moving the catheter 252 in a precise manner can be useful for various purposes, including those discussed further herein. Likewise, the catheter 252 can be directable according to various mechanisms and such as directing or pulling wires, directing or pulling signals, or any appropriate mechanism generally known in the art.

The device 252 can be used for various mechanisms and methods, such as delivering a material to a selected portion of the patient 204, such as within the cranium 288. The material can be any appropriate material such as a bioactive material, a pharmacological material, a contrast agent, or any appropriate material. As discussed further herein, the catheter device 252 can be precisely positioned via the navigation system 200 and otherwise used to achieve a protocol for positioning the material relative to the patient 204 in any appropriate manner, such as within the cranium 288. The device 252 may also include a brain probe to perform deep brain stimulation. The device 252 could then be tracked to navigate it along the determined trajectory to stimulate an anatomical target such as the STN.

The navigation system 200, or any appropriate navigation system, can be used with various frames that can assist in performing a procedure. Portions of the frame can be navigated or tracked with the navigation system 200 to assist in guiding navigated instruments. Various frames can include those described in U.S. patent application Ser. No. 10/651, 267, now U.S. Pat. App. Pub. 2005/0049486, referenced above. The stereotactic frames can allow for registration of patient space to a pre-acquired image to insure that the planned trajectory is achieved relative to the patient. In addition to various guided stereotactic frames, stereotactic frames can also include non-navigated frames or frames that can be used for determination of entry points, trajectories, and the like. Also, various stereotactic frames, such as the CRW offered by Radionics, Inc. may be utilized with the above-described guided procedure 18.

As briefly described above, the guided procedure 18 can be used to determine any appropriate type of procedure such as the frameless guided procedure in block 30, a stereotactic frame procedure in block 32, or an open procedure in block 34. These types of procedures can still take advantage of the guided procedure 18 substantially defined or described in blocks 23, 24, and 26. For example, the anatomical landmarks, anatomical targets, and planned trajectories can all be determined and then a procedure can be performed in any appropriate manner.

For example, with reference to block 30 of the guided procedure 18, a substantially frameless (i.e., without the use of a stereotactic frame) procedure can be performed. With brief reference to FIG. 8, a user, such as a physician, can determine that trajectory 132 is the most appropriate trajectory based upon the information relating to trajectory 132, the physician's experience, or any other appropriate reason. With reference to FIGS. 9 and 10, a user can view on a display 130, 228, or 225, the image data 46 of a selected region of the patient, such as the brain or cranium thereof. The display 130 can include an icon 132a, which can include a dashed line showing the proposed trajectory for the procedure. The user 282 can then guide the instrument 252 using the navigation elements, such as the tracking sensor 262 interconnected with the instruments 252 to allow the navigation system 200 to illustrate on the display 130 the path of the instrument 252.

Once the trajectory has been determined, including the entry point, the physician 282 can move the tracked instrument 252 relative to the patient 204, which has been registered to the image space as discussed above, to move the instruments 252 relative to the patient 204 and the determined entry point. It will be understood that the instrument 252 can be a plurality of instruments, such as a burr to form an entry port, a deep brain stimulation probe, or electrode to perform a procedure, or any other appropriate instrument that may be interchanged for various purposes. An icon, such as an arrow or a separate color, or a dark or solid line 132b can be illustrated relative to the image data 46 to illustrate the position of the instrument 252 relative to the image data 46 which correlates to the position of the instrument 252 relative to the patient 204.

As the physician 282 continues to move the instrument 252 relative to the patient, the icon 132b representing the position of the instrument 252 on the image data 46 can be shown to progress relative to the planned trajectory 132a which can also be illustrated on the image data 46. It will be understood that the icons 132a, 132b can be superimposed on the image data or the icons 132a, 132b can be displayed alone on the display 130 when performing an imageless procedure. It will be understood that the instrument 252 can be tracked with the icon 132b illustrating the position of the instrument 252 relative to the planned trajectory 132a. Various warnings can be provided, such as audible warnings, screen warnings, or the like to indicate when the instrument 252 is no longer on the planned trajectory 132a. Further, the navigation system 200, or a portion thereof, can provide various signals, such as audible or visible signals, when the instrument 252 reaches the selected anatomical target 129. Once the instrument 252 has reached the anatomical target 129, as illustrated by the icon 132b on the display 130, the procedure can proceed to the next step, such as the positioning of a probe, the stimulation of a portion of the brain, or any appropriate procedure.

Figure 11:
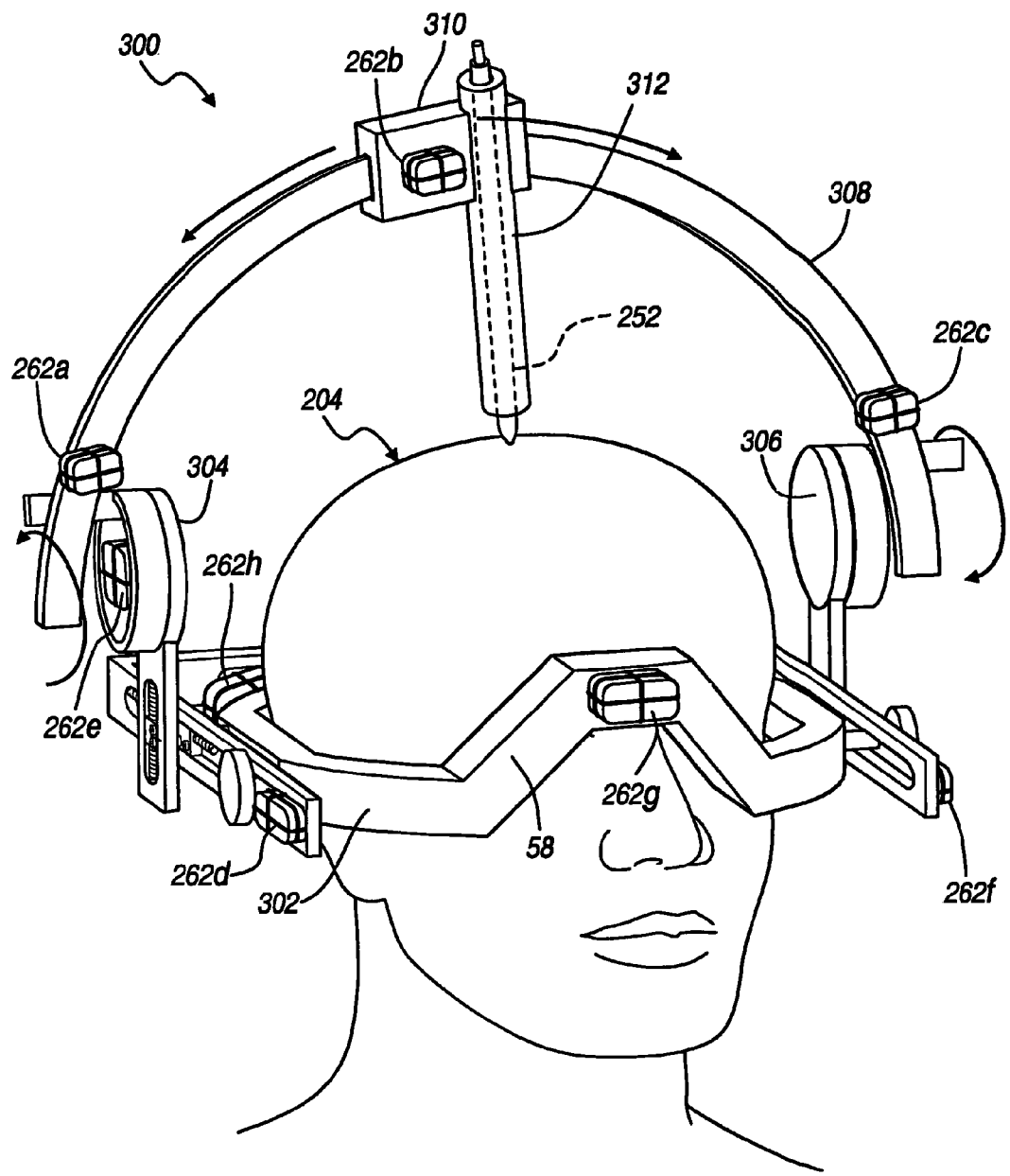
FIG. 11 is a detailed view of a patient in a stereotactic frame.

Although the procedure can proceed with a frameless scatter procedure in block 30, the procedure can also proceed relative or with a stereotactic frame as in block 32. Various stereotactic frames can include a stereotactic frame 300 illustrated in FIG. 11. The stereotactic frame 300 is generally described in U.S. patent application Ser. No. 10/651,267, now U.S. Pat. App. Pub. 2005/0049486, incorporated herein by reference. The stereotactic frame 300 will not be described in detail here, save for in relation to the guided procedure 18. Generally, the stereotactic frame 300 can include tracking sensors 262a-g. The various tracking sensors 262a-g can be provided to track the various portions of the stereotactic frame 300 relative to the patient 204. One or more of the tracking sensors 262a-g can be provided as a dynamic reference frame which can be interconnected with a first 302 that can be interconnected or positioned relative to the patient 204. Further, various interconnection mechanisms such as connection arms 304 and 306 can be interconnected to the first portion of the frame 302 which can be the base 256. Also a bow or arc 308 can be interconnected with the linkage arms 304, 306. The tracking sensors 262a-262g can allow for each of the various portions of the stereotactic frame 300 to be tracked with the navigation system 200. It will also be understood that the various linkages such as the linkage arms 304, 306 can be used to determine the position of the arc 308 relative to the patient 204.

The arc 308 can support a movable element 310 which includes a guide tube 312 provided therewith. The guide tube 312 can allow for passing or moving of the instrument 252 relative to the patient 204. As discussed above, the instrument 252 can include a probe, deep brain stimulation element, implant, etc. Nevertheless, the tracking sensor 262b can track the position of the movable element 310 relative to the patient 204 or the various tracking sensors 262a-g can provide more detailed information of the position of the guide tube 312 relative to the patient 204. Nevertheless, the navigation system 200, according to the guided procedure 18, can determine the position of the target, appropriate trajectories, and illustrate the same on the display 130 illustrated in FIG. 8, or the displays 225 and 228 (FIG. 9). The stereotactic frame 300 can then be provided to assist in guiding the instrument 252 relative to the patient 204. Although the display 130 can also display the icons illustrating the position of the planned trajectory 132a and the trajectory or current location of the instrument 252 in icon 132b, the stereotactic frame 300 can assist in guiding the instrument 252 to the appropriate target. The stereotactic frame 300 can also assist in determining whether the target has been reached by determining the trajectory of the instrument 252 with the guide tube 312, the distance passed through the guide tool 312, and other appropriate data.

Figure 12:
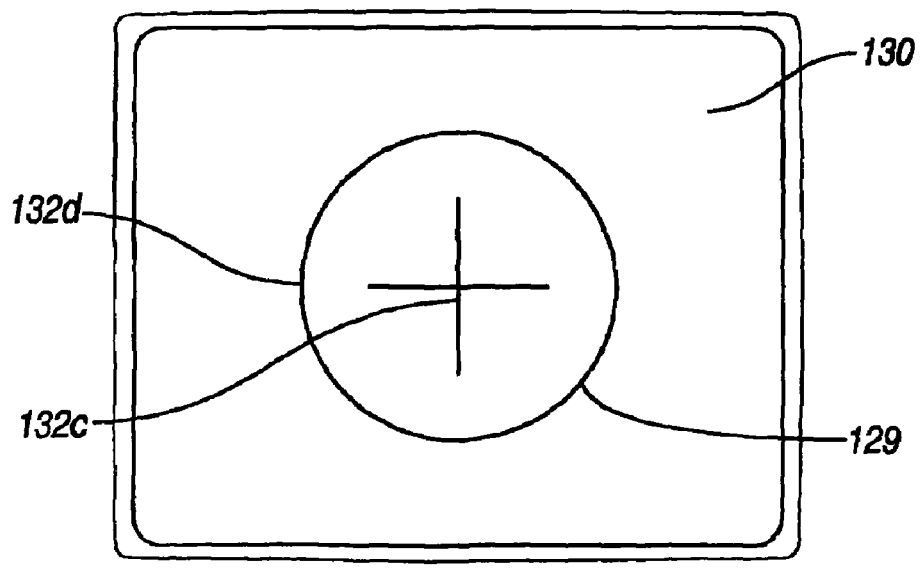
FIG. 12 is an exemplary view of the display 130 illustrating a navigation screen.

It will be understood that the position of the instrument 252 can be illustrated on the display 130, 225, 228 in any appropriate manner. Although the icon 132a can include a solid icon 132b represented or positioned relative to the planned trajectory 132a, it can also include a cross-hair 132c relative to a circle 132d. The cross-hair can represent the position of the instrument 252 and the circle 132d can represent the position or planned trajectory, as illustrated in FIG. 12. Therefore, it will be understood that the display 130, 225, 228 can display the information in any appropriate manner.

Also described is an open procedure block 34 that can be assisted with the guided procedure 18 for various purposes. Although a substantially open procedure in block 34 can generally allow for visualization of the brain by the physician 282, the guided procedure 18 may assist in helping the physician 282 to determine the anatomical target and a selected trajectory thereto. Thus, although the guided procedure may not be guided with a navigated system, the guided procedure 18 can assist the physician in determining the anatomical target and selecting an entry point, and even assist in selecting a trajectory to reach the anatomical target. Further, the various combinations of the systems can be provided, so that even a substantially unguided stereotactic frame can be used in the open procedure 34.

The above described methods and algorithms can also be used or executed by the navigation system, including the navigation processor and the planning processor to determine the anatomical landmarks, the anatomical targets, the trajectories, and the like. Also systems like the StimPilot™ system from Medtronic Navigation can be used to perform various computational and navigational functions. The above-described system can be provided as computer readable or computer executable instructions to assist a user in using the StimPilot™ system to provide for deep brain stimulation. For example, rather than requiring a user to determine the AC, PC and the mid-sagittal plane, the above-described method can be loaded onto the work station so that once the image data is appropriately entered into the system, such as merging the image data, processing the image data (in addition to that described above), StimPilot™ the system can then determine the anatomical landmarks and further determine the location of the anatomical targets, as described above. Also, the automatic and manual planning of a system can be further augmented by the determination of appropriate trajectories according other method described above. Nevertheless, a system, such as the StimPilot™ system from Medtronic Navigation, Inc., can be augmented with the navigated procedure 18 to assist in achieving a selected result.

What is claimed is:

1. A system to navigate a surgical plan relative to an anatomy, comprising:
   an instrument operable to assist in performing the surgical plan;
   a tracking device operable to be interconnected with the instrument;
   a tracking system operable to track the tracking device wherein a location of the instrument is operable to be determined at least in part based upon the tracked position of the tracking device;
   a planning processor operable to execute instructions configured to:
      process image data to segment a third ventricle in a brain in at least a sub-plurality of a plurality of slices of the image data, wherein the image data is obtained by an imaging system;
      align at least the sub-plurality of slices in the image data;
      after aligning at least the sub-plurality of the plurality of slices of the image data, determine a mid-sagittal plane based on the aligned sub-plurality of slices;
      after determining the mid-sagittal plane, determine at least one anatomical landmark, wherein the anatomical landmark includes at least one of an anterior commissure or a posterior commissure as a bright point in the image data at a boundary of the segmented third ventricle, where an intensity change at the edge of the segmented third ventricle that can be an edge where the at least one of the anterior commissure or the posterior commissure meet the third ventricle;
      after determining at least one anatomical landmark, determine an anatomical target, which is a functional target that is relatively indistinguishable from the surrounding structures, based upon the identified anatomical landmark; and
      after determining the anatomical target, determine a path through the anatomy based upon the image data of the anatomy to reach the determined anatomical target; and
   a display operable to display at least one of a planned path icon illustrating a planned path, an instrument icon illustrating the position of the instrument, an instrument path icon illustrating the entire path of the instrument at an instant in time, the image data of the anatomy, or combinations thereof.

2. The system of claim 1, wherein the tracking system includes a localizer.

3. The system of claim 2, wherein the tracking system includes at least one of an electromagnetic navigation system, an acoustic navigation system, an optical navigation system, an accelerometer navigation system, a radiation navigation system, or a radar navigation system.

4. The system of claim 1, wherein the instrument includes at least one of a sensor, a recorder, a probe, a stimulator, a catheter, a cannula, a deep brain stimulator, or combinations thereof.

5. The system of claim 1, further comprising:
   a navigation frame operable to be interconnected with the anatomy;
   wherein the navigation frame guides the instrument relative to the anatomy.

6. The system of claim 1, further comprising:
   the imaging system that obtains the image data of the anatomy that is accessed by the planning processor.

7. The system of claim 6, wherein the imaging system includes at least one of a magnetic resonance imaging system, a positron emission tomography system, an x-ray system, a computer tomography system, a single photon emission computer tomography, or a planar gamma tomography.

8. The system of claim 1, further comprising a memory system operable to store image data of the anatomy accessed by the planning processor, the plan, and procedure specific information.

9. The system of claim 8,
   wherein the stored plan includes the determined anatomical target which is an initial anatomical target;
   wherein the instrument includes at least a sensing device operable to sense the anatomy or physiology near the initial anatomical target;
   wherein the instructions are further configured to determine a refined anatomical target location by refining the location of the initial anatomical target based on sensed anatomy or physiology;
   wherein determine the path through the anatomy based upon the image data of the anatomy to reach the determined anatomical target includes determine a path to the refined anatomical target location.

10. The system of claim 1, wherein the planning processor operable to execute instructions is further configured to:
   after segmenting the third ventricle and before aligning at least the sub-plurality of slices of the image data, skeletonize a line in the segmented third ventricle in at least the sub-plurality of the plurality of slices of the image data;
   wherein determining the mid-sagittal plane is further based on the skeletonized line in the segmented third ventricle.

11. A system to navigate a surgical plan relative to an anatomy, comprising:
   an instrument operable to assist in performing the surgical plan;
   a tracking device operable to be interconnected with the instrument at a leading end of the instrument;
   a tracking system operable to track the tracking device wherein a location of the instrument is operable to be determined at least in part based upon the tracked position of the tracking device;
   an imaging system operable to obtain image data of the anatomy that includes a distinguishable anatomical landmark and a relatively indistinguishable anatomical target, wherein the image data of the anatomy includes a plurality of slices of image data of a brain;
   a planning processor operable to execute instructions configured to automatically:
      determine a third ventricle of the brain in at least a sub-plurality of the plurality of slices of the image data,
      after determining the third ventricle, skeletonize a line in the determined third ventricle;

after skeletonizing a line, aligning at least the sub-plurality of slices based on the skeletonized line;

after aligning at least the sub-plurality of slices, determine a mid-sagittal plane of the brain based at least on the skeletonized line, after determining a mid-sagittal plane, identify the distinguishable anatomical landmark in the image data;

after identifying the distinguishable anatomical landmark in the image data, determine the relatively indistinguishable anatomical target, which is relatively indistinguishable in the image data of the brain, based upon the identified distinguishable anatomical landmark;

determine an entry region into the anatomy to reach the determined relatively indistinguishable anatomical target;

weight the image data based on predetermined structures that are present in the image data;

determine a plurality of trajectories through the anatomy;

after determining the plurality of trajectories, determine a threshold trajectory from the determined plurality of trajectories based at least on the weighted image data; and determine a planned path through an anatomical region based at least on the determined threshold trajectory and the image data to reach the determined relatively indistinguishable anatomical target; and a display operable to display at least one of a planned path icon representing the planned path, an instrument icon illustrating the position of the instrument, an instrument path icon illustrating the entire path of the instrument at an instant in time, the image data of the anatomy, or combinations thereof.

12. The system of claim 11, wherein the tracking system includes at least one of an electromagnetic navigation system, an acoustic navigation system, an optical navigation system, an accelerometer navigation system, a radiation navigation system, or a radar navigation system.

13. The system of claim 11, wherein the instructions, prior to determining the third ventricle, are further configured to include segmenting a portion of the image data, removing unneeded data from the image data, smoothing the image data, or combinations thereof.

14. The system of claim 13, wherein the instrument includes a deep brain stimulator, a recording device, a probe, a cannula, or combinations thereof.

15. The system of claim 11, wherein the imaging system includes at least one of a magnetic resonance imaging system, an x-ray imaging system, a computer tomography imaging system, a positron emission tomography imaging system, an ultrasound imaging system, a single photon emission computer tomography system, or a planar gamma scintigraphy system.

16. The system of claim 11, wherein the
identifying the distinguishable anatomical landmark in the image data includes determine at least one of an anterior commissure or a posterior commissure in the aligned plurality of slices at a change in intensity from the determined third ventricle to the one of the anterior commissure or the posterior commissure.

17. The system of claim 11, further comprising:
a tracking frame operable to be positioned relative to the anatomy;
wherein the tracking device is interconnected with the tracking frame; and
a guide portion defined by the tracking frame and tracked with the tracking system, wherein the instrument is guided with the guiding portion relative to the anatomy.

18. The system of claim 17,
wherein the tracking device includes a first tracking device interconnected with the tracking frame and a second tracking device interconnected with the instrument;
wherein the tracking frame and the instrument can be tracked substantially independently relative to one another;
wherein the tracking frame can be fixed relative to the anatomy and the instrument can be tracked as it moves relative to the tracking frame and the anatomy.

19. The system of claim 11, further comprising:
a tracking system processor operable to execute instructions to determine a position of the tracking device.

20. A system to navigate a surgical plan relative to an anatomy, comprising:
a memory system operable to store a plurality of slices of image data of the anatomy;
a planning processor operable to execute instructions configured to:
process the image data to determine a third ventricle in a brain in the image data;
after determining the third ventricle, skeletonize a line in the determined third ventricle; and
after skeletonizing the line, determine a mid-sagittal plane from the skeletonized line;
after determining the mid-sagittal plane, determine a true axial plane through the image data with the mid-sagittal plane;
after determining the true axial plane, determine at least one anatomical landmark to include at least an anterior commissure or a posterior commissure as a bright point in the image data at a boundary of the determined third ventricle, where the intensity changes at the edge of third ventricle can be an edge where the at least one of the anterior commissure or the posterior commissure and the third ventricle meet;
after determining the at least one anatomical landmark, determine an anatomical target, which is a functional target that is relatively indistinguishable from the surrounding structures, based upon the determined anatomical landmark;
weight the image data regarding regions through which an instrument can pass;
determine an entry region into the anatomy;
determine a plurality of possible trajectories each with different entry points through the entry region of an instrument to the determined anatomical target; and
determine threshold trajectories from the determined plurality of possible trajectories of an instrument, wherein the determined threshold trajectories are determined at least based on the weighted image data and a respective individual trajectory from the determined plurality of possible trajectories of an instrument relative to portions of the weighted image data; and
a display device operable to illustrate at least the determined threshold trajectories;
wherein at least one of the determined threshold trajectories is saved to the memory as at least a portion of the surgical plan.

21. The system of claim 20, further comprising:
an instrument operable to assist in performing the surgical plan;
a tracking device operable to be interconnected with the instrument at a leading end of the instrument; and
a tracking system operable to track the tracking device wherein a location of the instrument is operable to be determined at least in part based upon the tracked position of the tracking device;
wherein the tracking system includes a navigation processor operable to determine the location of the instrument relative to the surgical plan;
wherein the display is further operable to display at least one of a trajectory icon illustrating at least one of the determined threshold trajectories, an instrument icon illustrating the navigated position of the instrument, a path icon illustrating the entire path of the instrument at an instant in time, and the image data of the anatomy.

22. The system of claim 21, wherein the instrument includes at least one of a deep brain stimulator, a probe, a recorder, a sensor, a cannula, or combinations thereof.

23. The system of claim 21, wherein the tracking system includes at least one of an electromagnetic navigation system, an acoustic navigation system, an optical navigation system, an accelerometer navigation system, a radiation navigation system, or a radar navigation system.

24. The system of claim 21, further comprising:
an imaging system operable to create the image data of the anatomy.

25. The system of claim 21, wherein the instrument includes:
a recorder operable to be positioned relative to a determined anatomical target;
wherein the recorder includes a sensor operable to sense an electrical activity; and
a communication system operable to transmit a signal based upon the electrical activity to the memory system;
wherein the planning processor is operable to determine a refined location of the anatomical target based on the transmitted signal and the tracked location of the recorder.

26. The system of claim 21, wherein the instrument is substantially flexible, substantially rigid, straight, curved, or combinations thereof.

27. The system of claim 21, further comprising:
a navigation frame;
wherein the navigation frame includes a guide portion interconnected with a frame electromagnetic tracking device;
wherein the guide portion is tracked with the tracking system via the frame electromagnetic tracking device and the instrument is moved relative to the guide portion.

28. The system of claim 27, wherein the tracking device includes an electromagnetic tracking device that includes a plurality of coils positioned at fixed angles relative to one another to provide at least 5 degree of freedom position information of the tracking device to the tracking system.

* * * * *